US009550022B2

(12) United States Patent
Brenneman et al.

(10) Patent No.: US 9,550,022 B2
(45) Date of Patent: Jan. 24, 2017

(54) METHODS, SYSTEMS AND DEVICES FOR TREATING HYPERTENSION

(71) Applicant: Rox Medical, Inc., San Clemente, CA (US)

(72) Inventors: Rodney Brenneman, San Juan Capistrano, CA (US); Brad Kellerman, San Clemente, CA (US); J. Christopher Flaherty, Auburndale, FL (US)

(73) Assignee: Rox Medical, Inc., San Clemente, CA (US)

( * ) Notice: Subject to any disclaimer, the term of this patent is extended or adjusted under 35 U.S.C. 154(b) by 0 days.

(21) Appl. No.: 14/668,733

(22) Filed: Mar. 25, 2015

(65) Prior Publication Data

US 2015/0196705 A1 Jul. 16, 2015

Related U.S. Application Data

(63) Continuation of application No. PCT/US2013/062458, filed on Sep. 27, 2013.

(Continued)

(51) Int. Cl.
*A61M 1/36* (2006.01)
*A61B 17/11* (2006.01)
*A61B 17/00* (2006.01)

(52) U.S. Cl.
CPC ............. *A61M 1/3655* (2013.01); *A61B 17/11* (2013.01); *A61B 2017/00367* (2013.01); *A61B 2017/1107* (2013.01); *A61B 2017/1139* (2013.01)

(58) Field of Classification Search
CPC ................... A61B 17/11; A61B 2017/00367; A61B 2017/1107; A61B 2017/1139; A61M 1/3655
See application file for complete search history.

(56) References Cited

U.S. PATENT DOCUMENTS 5,682,906 A 11/1997 Sterman et al.
7,828,814 B2 11/2010 Brenneman et al.
(Continued)

FOREIGN PATENT DOCUMENTS

CN 1218414 A 6/1999
CN 202169006 U 3/2012
(Continued)

OTHER PUBLICATIONS

International search report and written opinion dated Jan. 8, 2014 for PCT/US2013/062458.
(Continued)

*Primary Examiner* — Jacqueline Stephens
*Assistant Examiner* — Benjamin Klein
(74) *Attorney, Agent, or Firm* — Wilson, Sonsini, Goodrich & Rosati

(57) ABSTRACT

Provided is a method of treating arterial hypertension in a patient. The method comprises selecting a patient suffering from arterial hypertension and creating a flow pathway between a first vascular location and a second vascular location. The first vascular location comprises a source of arterial blood and the second vascular location comprises a source of venous blood. The method causes a reduction in diastolic pressure and a reduction in systolic pressure; and the reduction in diastolic pressure is to an extent at least approximating the reduction in systolic pressure. Systems and devices for creating a flow pathway are also provided.

12 Claims, 10 Drawing Sheets

Related U.S. Application Data

(60) Provisional application No. 61/707,280, filed on Sep. 28, 2012.

(56) References Cited

U.S. PATENT DOCUMENTS

| | | |
|---|---|---|
| 8,016,782 B2 | 9/2011 | Brenneman et al. |
| 8,641,747 B2 | 2/2014 | Brenneman et al. |
| 8,926,545 B2 | 1/2015 | Brenneman et al. |
| 2003/0014061 A1 | 1/2003 | Houser et al. |
| 2004/0158143 A1* | 8/2004 | Flaherty et al. .............. 600/407 |
| 2004/0236360 A1 | 11/2004 | Cohn et al. |
| 2004/0249335 A1 | 12/2004 | Faul et al. |
| 2005/0075656 A1* | 4/2005 | Beaupre ........................ 606/153 |
| 2005/0277965 A1 | 12/2005 | Brenneman et al. |
| 2008/0119879 A1 | 5/2008 | Brenneman et al. |

FOREIGN PATENT DOCUMENTS

| | | |
|---|---|---|
| CN | 102458303 A | 5/2012 |
| EP | 1520532 A2 | 4/2005 |
| WO | WO 2004/091696 A1 | 10/2004 |
| WO | WO 2005/075655 A2 | 8/2005 |
| WO | WO 2005/122919 A2 | 12/2005 |
| WO | WO 2012/034108 A1 | 3/2012 |
| WO | WO 2014/052919 A1 | 4/2014 |

OTHER PUBLICATIONS

European search report and opinion dated Jul. 21, 2015 for EP Application No. 13840519.6.

\* cited by examiner

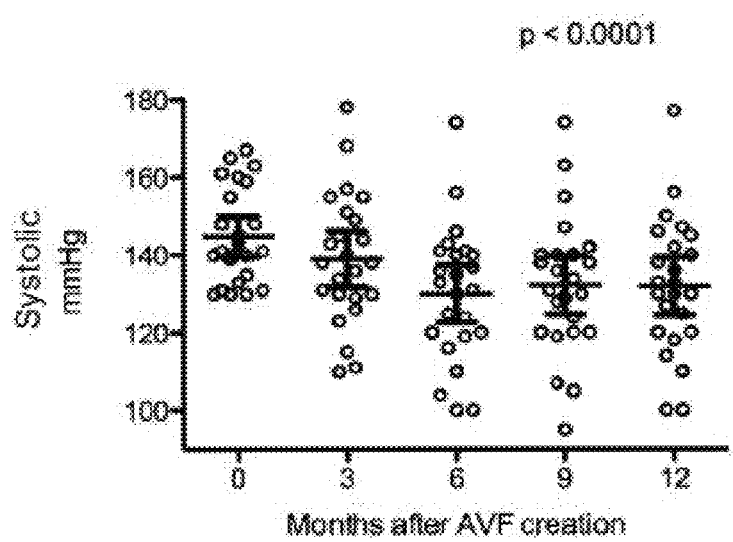

FIG 3E

Systolic blood pressure recordings at baseline (0) and at 3, 6, 9, and 12 months after creation of an iliac arteriovenous anastomosis using an anastomotic coupler device (Rox Medical, San Clemente, CA) ($p<0.0001$, by ANOVA). Means and 95% Confidence Intervals at each time point are indicated by error bars. Post analysis testing revealed a differences between baseline and 3 months, baseline and 6 months, baseline and 9 months, baseline and 12 months, and between 3 months and 12 months.

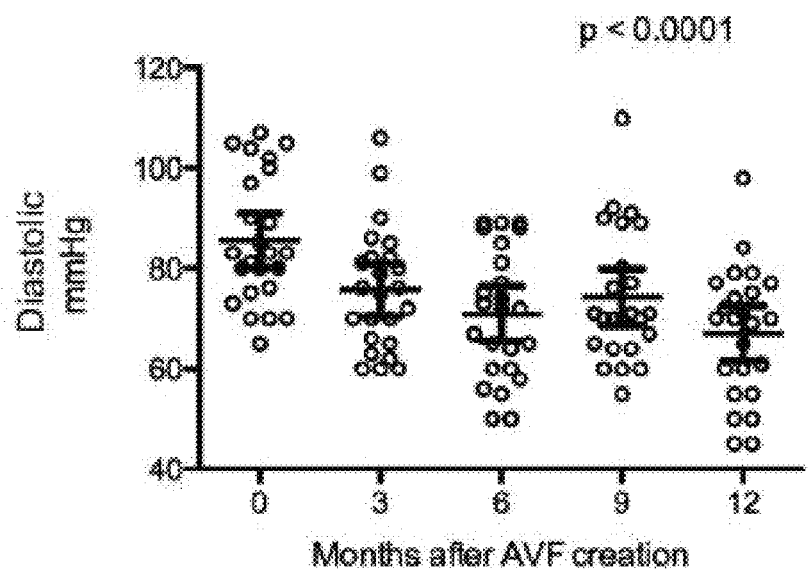

FIG 3F

Diastolic blood pressure recordings at baseline (0) and 3, 6, 9, and 12 months after creation of an iliac arteriovenous anastomosis using an anastomotic coupler device (Rox Medical, San Clemente, CA) (p<0.0001, by ANOVA). Means and 95% Confidence Intervals at each time point are indicated by error bars. Post analysis testing revealed significant differences between baseline and 6 months, baseline and 9 months, and baseline and 12 months.

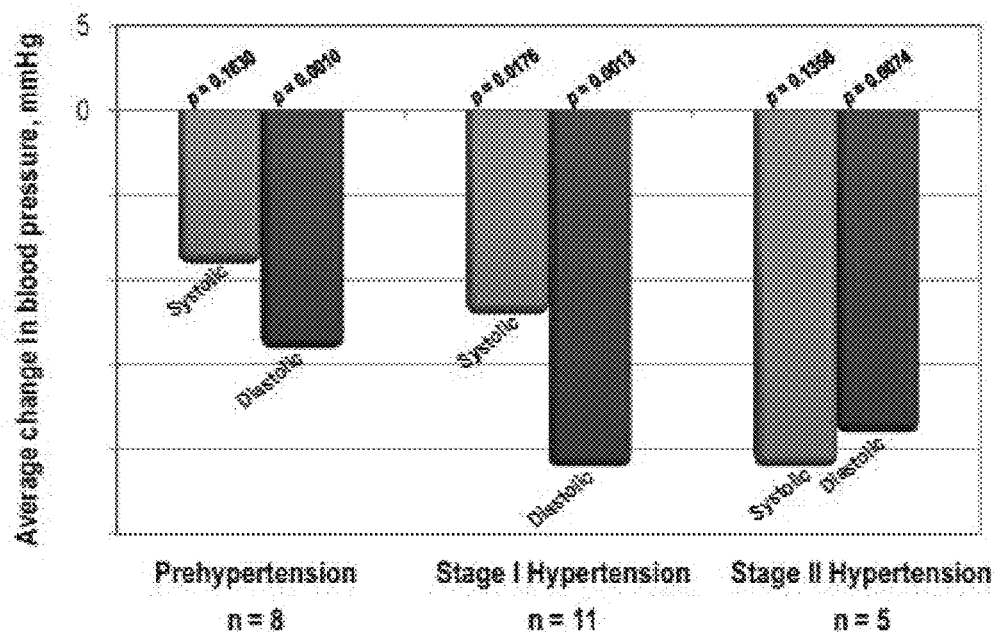

FIG 4

Histogram of the change in clinic based systolic and diastolic blood pressure measurements at 12 months according to stage of hypertension: pre-hypertension subjects (n = 8) had a baseline systolic blood pressure between 130 mmHg and 139 mmHg, Stage I hypertension subjects had baseline systolic blood pressure between 140 mmHg and 159 mmHg (n = 11), and Stage II hypertension subjects had a baseline systolic blood pressure greater than or equal to 160 mmHg (n = 5). At 12 months the reductions in systolic blood pressure recordings were 9 mmHg (p = ns), 12 mmHg (p = 0.02), and 21 mmHg (p = ns), respectively, while the changes in diastolic blood pressure recordings were 14 mmHg (p = 0.001), 21 mmHg (p = 0.001), and 19 mmHg (p = 0.01), respectively.

METHODS, SYSTEMS AND DEVICES FOR TREATING HYPERTENSION

CROSS-REFERENCE TO RELATED APPLICATIONS

This application is a continuation of International Patent Application No. PCT/US2013/062458, filed Sep. 27, 2013, which claims the benefit of U.S. Provisional Application No. 61/707,280, entitled Methods, Systems and Devices for Treating Hypertension, filed Sep. 28, 2012, the entire contents of which are incorporated herein by reference in their entirety. This application is related to: U.S. Pat. No. 7,828,814, entitled "Device and Method for Establishing an Artificial Arterio-Venous Fistula", filed Apr. 4, 2007; U.S. Non-Provisional application Ser. No. 11/152,621, entitled "Devices for Arterio-Venous Fistula Creation", filed Jun. 13, 2005; U.S. Non-Provisional application Ser. No. 11/151,802, entitled "Methods for Providing Oxygenated blood to Venous Circulation", filed Jun. 13, 2005; U.S. Non-Provisional application Ser. No. 11/946,454, entitled "Devices, Systems, and Methods for Creation of a Peripherally Located Fistula", filed Nov. 28, 2007; U.S. Non-Provisional application Ser. No. 12/017,437, entitled "Devices, Systems, and Methods for Peripheral Arteriovenous Fistula Creation", filed Jan. 22, 2008; U.S. Non-Provisional application Ser. No. 12/752,397, entitled "Device and Method for Establishing an Artificial Arteriovenous Fistula", filed Apr. 1, 2010; U.S. Non-Provisional application Ser. No. 12/905,412, entitled "Devices, Systems, and Methods for Enhanced Visualization of the Anatomy of a Patient", filed Oct. 15, 2010; the contents of each are incorporated by reference in their entirety.

TECHNICAL FIELD

The embodiments disclosed herein relate generally to systems, devices and methods for treating a patient, particularly a patient afflicted with arterial hypertension.

BACKGROUND

Hypertension is a chronic medical condition in which the blood pressure in the arteries is elevated requiring the heart to work harder to circulate blood through the vessels. Blood pressure includes two measurements, systolic and diastolic, which depend on whether the heart muscle is contracting (systole) or relaxed between beats (diastole). Normal blood pressure at rest is within the range of 100-400 mmHg systolic and 60-90 mmHg diastolic. High blood pressure is typically present if it is persistently at or above 140/90 mmHg.

Hypertension is a major risk factor for stroke, myocardial infarction, heart failure, aneurysms of the arteries such as aortic aneurysms, peripheral arterial disease, and is a cause of chronic kidney disease. Even moderate elevation of arterial blood pressure is associated with a shortened life expectancy.

Current treatment methods, such as the administration of pharmaceuticals and renal denervation therapy, are associated with incomplete or otherwise limited treatment; high cost; invasiveness; and numerous undesirable side effects. There is therefore a need for improved approaches, including both devices and methods, for treating patients suffering from hypertension.

SUMMARY

According to one aspect of the present inventive concepts, a method for treating hypertension in a patient comprises selecting a patient suffering from arterial hypertension and creating a flow pathway between a first vascular location and a second vascular location, where the first vascular location comprises a source of arterial blood and the second vascular location comprises a source of venous blood, where the method is constructed and arranged to cause a reduction in diastolic pressure and a reduction in systolic pressure, and where the reduction in diastolic pressure is to an extent at least approximating the reduction in systolic pressure. Arterial hypertension can comprise systemic arterial hypertension.

The method can be further constructed and arranged to treat a patient disease or disorder selected from the group consisting of: chronic obstructive pulmonary disease, congestive heart failure, lung fibrosis, adult respiratory distress syndrome; lymphangioleiomytosis; pulmonary hypertension; sleep apnea such as sleep apnea due to hypoxemia or hypertension; and combinations of these.

The method can be constructed and arranged to cause a decrease in vascular resistance, for example a decrease in peripheral vascular resistance such as infrarenal vascular resistance. The method can be further constructed and arranged to cause a physiologic change in the patient selected from the group consisting of: increased oxygen delivery by the arterial system; increased blood volume; increased proportion of blood flow to the descending aorta; increased blood flow to the kidneys; increased blood flow outside the kidneys; increased cardiac output; and combinations of these. The method can be further constructed and arranged to minimize chronic increase in heart rate. The method can be further constructed and arranged to minimize a decrease in cardiac function. The method can be further constructed and arranged to minimize adverse effects to a kidney of the patient. The method can be further constructed and arranged to cause at least one of an increase in oxygenation or an increase in flow rates associated with the patient's chemo-receptors. The method can be further constructed and arranged to modify the patient's central sympathetic tone. The modification to the patient's central sympathetic tone can cause a reduction in at least one of systolic or diastolic blood pressure. The modification to the patient's central sympathetic tone can provide a therapeutic benefit to a patient disease or disorder selected from the group consisting of: diabetes; sleep apnea; heart failure; and combinations of these.

The reduction in diastolic pressure can be greater than the reduction in systolic pressure. For example, the reduction in diastolic pressure can be at least 2 mmHg more than the reduction in systolic pressure, or at least 4 mmHg more than the reduction in systolic pressure, or approximately 5 mmHg more than the reduction in systolic pressure.

The reduction in diastolic pressure can be at least 5 mmHg, or at least 10 mmHg, or at least 15 mmHg, or at least 18 mmHg. The reduction in systolic pressure can be at least 5 mmHg, or at least 10 mmHg, or at least 13 mmHg.

The reduction in diastolic pressure can correlate to the diastolic pressure present prior to the creation of the flow pathway. For example, the reduction in diastolic pressure can be proportional to the diastolic pressure present prior to the creation of the flow pathway.

The flow pathway can comprise a fistula. The flow pathway can be positioned relatively proximate a kidney of the patient. The flow pathway can be positioned at a location that is infrarenal.

The first vascular location can comprise an artery selected from the group consisting of: aorta; axillary; brachial; ulnar; radial; profundal; femoral; iliac; popliteal; and carotid. The second vascular location can comprise a vein selected from the group consisting of: inferior vena cava; saphenous; femoral; iliac; popliteal; brachial; basilic; cephalic; medial forearm; medial cubital; axillary; and jugular.

The first vascular location can comprise a chamber of the heart. In some embodiments, the first vascular location comprises the left atrium and the second vascular location comprises the right atrium. In some embodiments, the first vascular location comprises the left ventricle and the second vascular location comprises the coronary sinus. In some embodiments, the first vascular location comprises the aorta and the second vascular location comprises a vein, and the flow pathway can comprise a graft positioned between the aorta and the vein.

The method can further comprise dilating the flow pathway. The flow pathway can be dilated by inflating a balloon in the flow pathway. The dilation can be performed at a diameter between 3 mm and 5 mm, such as at a diameter of approximately 4 mm.

The method can further comprise performing a flow pathway assessment procedure. The flow pathway assessment procedure can comprise performing an anatomical measurement, for example a measurement selected from the group consisting of: a flow pathway diameter measurement; a flow pathway length measurement; a measurement of the distance between an artery and vein comprising the flow pathway; a measurement of the distance between the flow pathway and a vessel sidebranch; and combinations of these. The flow pathway assessment procedure can comprise performing an assessment of at least one of flow in the flow pathway or flow proximate the flow pathway, for example a flow assessment selected from the group consisting of: flow through the flow pathway; flow in a vessel segment proximate the flow pathway; flow measured using Doppler Ultrasound; flow measured using angiographic techniques; and combinations of these. The flow pathway assessment procedure can comprise an assessment of a patient physiologic condition, for example a condition selected from the group consisting of: cardiac output; blood pressure such as systolic and/or diastolic blood pressure; respiration; a blood gas parameter; blood flow; vascular resistance; pulmonary resistance; an average clotting time assessment; serum creatinine level assessment; and combinations of these.

The method can further comprise placing an implant in the flow pathway. The implant can comprise an anastomotic clip. The implant can comprise an implant selected from the group consisting of: suture; staple; adhesive; and combinations of these. The implant can comprise at least a portion that is biodegradable.

The method can further comprise modifying the flow pathway. The modification can comprise dilating at least a portion of the flow pathway. In an embodiment, where the method further comprises placing an anastomotic clip in the flow pathway, the modification can be performed after the placement of the anastomotic clip. The modification can be performed at least one week after the creating of the flow pathway. The modification can comprise modifying a flow parameter selected from the group consisting of: flow pathway cross sectional diameter; flow pathway average cross sectional diameter; flow pathway flow rate; flow pathway average flow rate; diastolic pressure after flow pathway creation; diastolic pressure change after flow pathway creation (e.g. as compared to diastolic pressure prior to flow pathway creation); systolic pressure after flow pathway creation; systolic pressure change after flow pathway creation (e.g. as compared to systolic pressure prior to flow pathway creation); ratio of diastolic to systolic pressure after flow pathway creation; difference between diastolic pressure and systolic pressure after flow pathway creation; and combinations of these. The modification can comprise a flow modification procedure selected from the group consisting of: increasing flow through the flow pathway; decreasing flow through the flow pathway; increasing the diameter of at least a segment of the flow pathway; decreasing the diameter of at least a segment of the flow pathway; removing tissue proximate the flow pathway; blocking a sidebranch proximate the flow pathway; and combinations of these.

The method can further comprise creating a second flow pathway between a third vascular location and a fourth vascular location. The first vascular location can comprise an artery and the third vascular location can comprise the same artery. The second vascular location can comprise a vein and the fourth vascular location can comprise the same vein. The second flow pathway can comprise a fistula. The second flow pathway can be created at least twenty four hours after the creation of the first flow pathway.

According to another aspect of the present inventive concepts, a system for treating hypertension in a patient comprises a needle delivery device constructed and arranged to place a vessel-to-vessel guidewire from a starting vessel to a target vessel and a flow creation device constructed and arranged to be advanced over the vessel-to-vessel guidewire and to create a flow pathway between the starting vessel and the target vessel, where the system is constructed and arranged to cause a reduction in diastolic pressure.

The system can be further constructed and arranged to treat a patient disease or disorder selected from the group consisting of: chronic obstructive pulmonary disease, congestive heart failure, lung fibrosis, adult respiratory distress syndrome; lymphangioleiomytosis; pulmonary hypertension; sleep apnea such as sleep apnea due to hypoxemia or hypertension; and combinations of these.

The system can be further constructed and arranged to cause a reduction in systolic blood pressure. The system is further constructed and arranged to cause a reduction in diastolic pressure to an extent at least approximating a reduction in systolic pressure. The system can be further constructed and arranged to cause a reduction in diastolic pressure to an extent greater than a reduction in systolic pressure.

The needle delivery device can comprise an advanceable needle. The needle delivery device can comprise a needle with a gauge between 20 and 24, such as an approximately 22 gauge needle. The needle delivery device can comprise a curved needle. The needle delivery device can further comprise a marker indicating the direction of curvature of the curved needle, for example a marker selected from the group consisting of: flat surface, visible marker, line, textured surface, and combinations of these. The needle delivery device can further comprise a sheath constructed and arranged to slidingly receive the curved needle. The needle can comprise a proximal end and a hub positioned on said proximal end. The hub can be constructed and arranged to be advanced to advance the curved needle out of the sheath. The needle delivery device can comprise a needle comprising a shaped memory alloy, for example a nickel titanium alloy.

The system can further comprise a vessel-to-vessel guidewire constructed and arranged to be placed from the starting vessel to the target vessel by the needle delivery device. The vessel-to-vessel guidewire can comprise a wire with an outer diameter approximating 0.018". The vessel-to-vessel guidewire can comprise a marker, for example a marker positioned to indicate the fistula location. The vessel-to-vessel guidewire can comprise a distal portion and a mid portion, where the mid portion can comprise a construction different than the construction of the distal portion, for example the mid portion can comprise a stiffness greater than the stiffness of the distal portion.

The flow creation device can comprise a balloon catheter configured to dilate tissue positioned between the first vascular location and the second vascular location. The flow creation device can comprise an energy delivery device constructed and arranged to deliver energy to tissue positioned between the first vascular location and the second vascular location.

The flow creation device can comprise a clip deployment catheter comprising an anastomotic clip. The clip deployment catheter can comprise a handle, and the handle can comprise a control constructed and arranged to deploy the anastomotic clip. The control can comprise a button. The handle can comprise a safety position for the control, for example, the handle can comprise a longitudinal axis, and the control can be constructed and arranged to be moved relatively perpendicular to said longitudinal axis to transition from the safety position to a first ready to deploy position. The clip can comprise at least two distal arms, and the handle can be constructed and arranged to allow an operator to move the control from a first ready to deploy position to a first deployed position, where the movement causes the at least two distal arms to be deployed. The handle can comprise a longitudinal axis, and the control can be moved relatively parallel to said longitudinal axis to transition from the first ready to deploy position to the first deployed position. The handle can be constructed and arranged to allow an operator to move the control from the first deployed position to a second ready to deploy position. The control can be moved relatively perpendicular to the longitudinal axis to transition from the first deployed position to the second ready to deploy position. The clip can comprise at least two proximal arms, and the handle can be constructed and arranged to allow an operator to move the control from the second ready to deploy position to a second deployed position, where the movement causes the at least two proximal arms to be deployed. The control can be moved relatively parallel to said longitudinal axis to transition from the second ready to deploy position to the second deployed position.

The clip deployment catheter can comprise an outer sheath, and the control can be constructed and arranged to be moved from a first position to a second position to cause movement of the outer sheath. The clip deployment catheter can be constructed and arranged such that movement of the control to the second position causes a tactile feedback event to occur. The clip can comprise multiple deployable arms, and the clip deployment catheter can be constructed and arranged such that movement of the control to the second position causes at least one arm to be deployed.

At least one of the clip deployment catheter or the clip can comprise at least one marker constructed and arranged to rotationally position the clip. The marker can be constructed and arranged to be oriented toward the target vessel prior to deployment of the clip. The marker can be oriented based on a patient image, for example a real-time fluoroscopy image. The clip can comprise a swing arm for deployment in the target vessel, and the marker can be positioned in alignment with the swing arm. The clip deployment catheter can comprise a distal portion and said distal portion can comprise the clip and the marker, for example where the marker is proximate the clip. The clip deployment catheter can comprise a proximal portion and said proximal portion can comprise the marker, for example the clip deployment catheter can comprise a handle and the marker can be positioned on the handle.

At least one of the clip deployment catheter or the clip can comprise at least one marker constructed and arranged to longitudinally position the clip at the fistula location. The marker can indicate the distal and/or proximal end of the clip.

The clip can comprise multiple deployable arms, and the clip deployment catheter can be constructed and arranged to deploy at least one of said deployable arms and subsequently recapture said one of said deployable arms.

The clip deployment catheter can be constructed and arranged to be rotated and simultaneously deployed from the starting vessel to the target vessel over the vessel-to-vessel guidewire.

The clip deployment catheter can comprise a projection constructed and arranged to mechanically engage the clip. The projection can comprise a pin. The clip deployment catheter can further comprise a second projection constructed and arranged to mechanically engage the clip.

The system can further comprise a flow pathway maintaining implant. The flow pathway maintaining implant can comprise an anastomotic clip. The clip can comprise a plurality of distal arms and a plurality of proximal arms, where the distal arms can be independently deployable from the proximal arms. In some embodiments, the clip comprises four deployable distal arms and four deployable proximal arms. The clip can comprise nickel titanium alloy. The clip can comprise multiple deployable arms, and at least two arms can comprise a marker, for example a radiopaque marker. The flow pathway maintaining implant can comprise suture; one or more staples; adhesive; at least a portion that comprises biodegradable material; and combinations of these.

The system can further comprise a venous system introducer. The venous system introducer can be constructed and arranged to access the starting vessel. The venous system introducer can comprise an 11 French introducer. The venous system introducer can comprise a beveled distal tip, for example comprising an angle between 20° and 50°, such as an angle of approximately 30°. The venous system introducer can comprise a marker proximate the beveled distal tip, for example a radiopaque marker. The venous system introducer can comprise a proximal portion comprising a marker, where the marker can be aligned with the beveled distal tip. The venous system introducer can comprise a distal portion and an expandable element mounted to the distal portion, for example where the expandable element comprises a balloon. The expandable element can be constructed and arranged to prevent inadvertent advancement of the introducer into the target vessel. The venous system introducer can be constructed and arranged to stabilize the starting vessel.

The system can further comprise an arterial system introducer. The arterial system introducer can be constructed and arranged to access the target vessel. The arterial system introducer can comprise a 4 French introducer.

The system can further comprise a target wire constructed and arranged for positioning in the target vessel. The target wire can comprise a helical distal portion. The target wire can comprise a radiopaque distal portion.

The system can further comprise a flow pathway modifying device. The flow pathway modifying device can comprise an expandable element. The expandable element can be constructed and arranged to expand to a diameter between 3 mm and 5 mm, such as a diameter of approximately 4 mm. The expandable element can comprise a balloon. The expandable element can comprise at least one of an expandable cage or radially deployable arms. The flow modifying device can comprise a device selected from the group consisting of: an over the wire device constructed and arranged to be delivered over a vessel-to-vessel guidewire as described herein; an expanding scaffold configured to increase or otherwise modify flow pathway geometry such as an expandable balloon; an energy delivery catheter such as a catheter configured to deliver energy to tissue proximate a flow pathway; an agent delivery catheter such as a catheter configured to deliver an agent such as a pharmaceutical agent or an adhesive such as fibrin glue; and combinations of these.

The system can further comprise a patient imaging apparatus. The patient imaging apparatus can comprise a fluoroscope and/or an ultrasound imager.

According to another aspect of the present inventive concepts, a system for creating a fistula between a starting vessel and a target vessel at a fistula location in a patient comprises a vascular introducer; a needle delivery device; a vessel-to-vessel guidewire constructed and arranged to be placed from the starting vessel to the target vessel by the needle delivery device; an anastomotic clip; and a clip deployment catheter constructed and arranged to deploy the anastomotic clip.

The system can be further constructed and arranged to treat a patient disease or disorder selected from the group consisting of: chronic obstructive pulmonary disease, congestive heart failure, lung fibrosis, adult respiratory distress syndrome; lymphangioleiomytosis; pulmonary hypertension; sleep apnea such as sleep apnea due to hypoxemia or hypertension; and combinations of these.

BRIEF DESCRIPTION OF THE DRAWINGS

The accompanying drawings, which are incorporated in and constitute a part of this specification, illustrate various embodiments of the present inventive concepts, and, together with the description, serve to explain the principles of the invention. In the drawings:

FIGS. 3E and 3F are a graph of blood pressure measurements recorded from patients receiving a flow pathway, consistent with the present inventive concepts.

FIG. 4 is a table of average change in blood pressure recorded from patients receiving a flow pathway, consistent with the present inventive concepts.

FIGS. 6A, 6B and 6C are anatomical views of three different needle trajectory paths, consistent with the present inventive concepts.

DETAILED DESCRIPTION OF THE DRAWINGS

Figure 1:
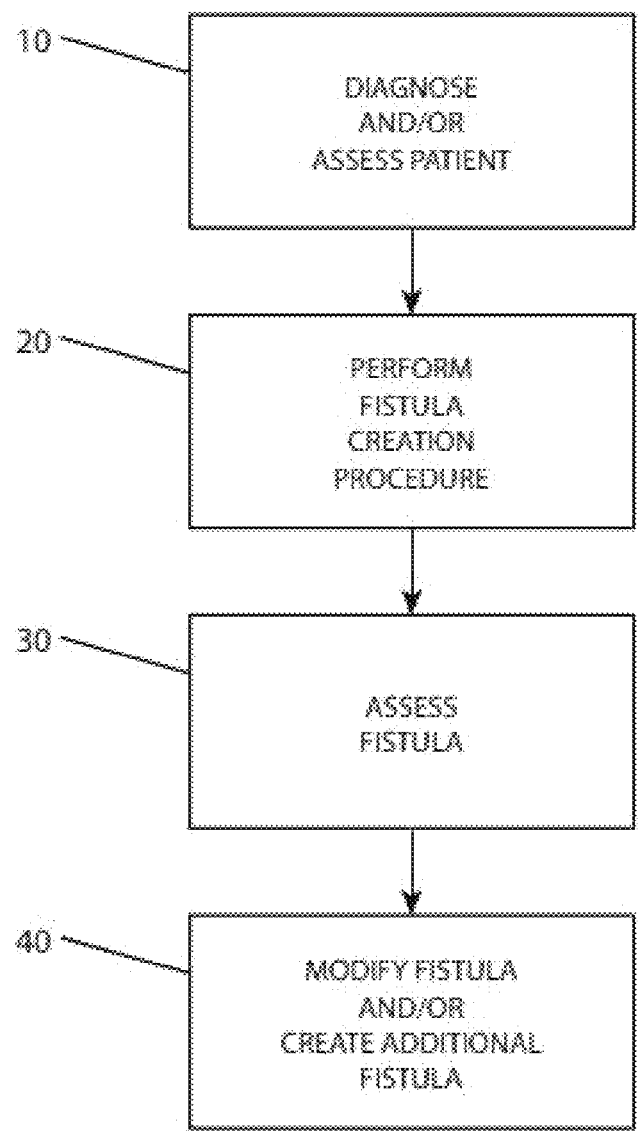
FIG. 1 is a flow chart of a method for treating a patient by creating a flow pathway between a first vascular location and a second vascular location, consistent with the present inventive concepts.

Reference will now be made in detail to the present embodiments of the inventive concepts, examples of which are illustrated in the accompanying drawings. Wherever practical, the same reference numbers will be used throughout the drawings to refer to the same or like parts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Referring now to FIG. 1, a flow chart for selecting and treating a patient by creating a fistula or other flow pathway between a first vascular location in the patient's arterial system and a second vascular location in the patient's venous system is illustrated, consistent with the present inventive concepts. In STEP 10, a patient assessment is performed, such as to diagnose the patient and determine if a fistula should be created in the patient. A patient can be selected based on a disease or disorder which is diagnosed in STEP 10 or previously. In some embodiments, a patient diagnosed with hypertension is selected to receive a fistula. Alternatively or additionally, a patient selected to receive a fistula can have a disease or disorder selected from the group consisting of: chronic obstructive pulmonary disease (COPD), congestive heart failure, lung fibrosis, adult respiratory distress syndrome; lymphangioleiomytosis; pulmonary hypertension; sleep apnea such as sleep apnea due to hypoxemia or hypertension; and combinations of these.

In STEP 20, a fistula creation procedure is performed on the patient. In some embodiments, the fistula creation procedure is performed as described in reference to FIG. 5 herebelow. In some embodiments, the fistula creation procedure is performed using a system of devices and components similar to system 100 of FIG. 2 described herebelow. The fistula is created between a first vascular location in the arterial system, such as an artery, and a second vascular location in the venous system, such as a vein. The fistula creation procedure can include the placement of a vessel-to-vessel guidewire between a starting vessel such as a vein, and a target vessel such as an artery. In these embodiments, the fistula can be created using one or more fistula creation devices that are advanced over the vessel-to-vessel guidewire. An anastomotic clip or other implant can be placed into the fistula via a clip placement device advanced over the vessel-to-vessel guidewire. Alternatively, a fistula can be created without an anastomotic clip, such as through the use of energy (e.g. radiofrequency energy), suture or staple (e.g. via an over-the-wire suture or staple delivery device), and/or a tissue treatment such as an adhesive (e.g. fibrin glue) coating of the tissue surrounding or otherwise proximate the fistula. One or more fistula treatment or modification procedures can be performed using fistula treatment or modification devices advanced over the vessel-to-vessel guidewire, such as a fistula modification performed in STEP 40 herebelow.

In some embodiments, a fistula or other flow pathway is created between an artery and a vein at a location distal to the renal arteries (i.e. an infrarenal location). In some embodiments, a fistula or other flow pathway is created proximate a kidney. Numerous locations for the fistula or other flow pathway can be selected, such as a fistula located between an artery and vein as described in reference to FIG. 5 herebelow. Alternatively or additionally, a flow pathway can be created between a chamber of the heart and a second vascular location, such as between the left atrium and the right atrium or between the left ventricle and the heart's coronary sinus. Alternatively or additionally, arterial blood can be diverted to the venous system by way of a flow pathway comprising a bypass graft, such as is described in applicant's co-pending application U.S. Non-Provisional application Ser. No. 11/151,802, entitled "Methods for Providing Oxygenated Blood to Venous Circulation", filed Jun. 13, 2005, the contents of which are incorporated by reference herein in its entirety.

During the fistula creation procedure and/or in a subsequent fistula modification procedure, a fistula dilation procedure can be performed. In some embodiments, an anastomotic clip is placed in the fistula and a balloon catheter is used to dilate the fistula and anastomotic clip simultaneously. In some embodiments, the balloon comprises a diameter of approximately 3 mm to 5 mm, such as a diameter of approximately 4 mm.

In STEP 30, a fistula assessment procedure can be performed. STEP 30 can be performed in the same clinical procedure as STEP 20, and/or in a subsequent clinical procedure such as a procedure at least twenty-four hours after completion of STEP 20, or at least 1 week, at least 1 month, and/or at least 6 months after completion of STEP 20. In some embodiments, the assessment performed in STEP 30 includes one or more anatomical measurements, such as a measurement selected from the group consisting of: a fistula diameter measurement; a fistula length measurement; a measurement of the distance between the artery and vein comprising the fistula; a measurement of the distance between the fistula and a vessel sidebranch; and combinations of these. In some embodiments, the assessment performed in STEP 30 comprises an assessment of flow, such as a flow assessment selected from the group consisting of: flow through the fistula; flow in a vessel segment proximate the fistula; flow measured using Doppler Ultrasound; flow measured using angiographic techniques; and combinations of these. In some embodiments, the assessment performed in STEP 30 comprises an assessment of a patient physiologic condition, such as an assessment of a physiologic condition selected from the group consisting of: cardiac output; blood pressure such as systolic and/or diastolic blood pressure; respiration; a blood gas parameter; blood flow; vascular resistance; pulmonary resistance; an average clotting time assessment; serum creatinine level assessment; and combinations of these.

In STEP 40, one or more fistula parameters can be modified. STEP 40 can be performed in the same clinical procedure as STEP 20, and/or in a subsequent clinical procedure such as a procedure at least twenty-four hours after completion of STEP 20, or at least 1 week, at least 1 month, and/or at least 6 months after completion of STEP 20. In some embodiments, STEP 30 and STEP 40 are performed in the same clinical procedure (e.g. both in the same clinical procedure as STEP 20 or both in a subsequent clinical procedure). In some embodiments, one or more patient or fistula parameters to be modified are selected from the group consisting of: fistula cross sectional diameter; fistula average cross sectional diameter; fistula flow rate; fistula average flow rate; diastolic pressure after fistula creation; diastolic pressure change after fistula creation (e.g. as compared to diastolic pressure prior to fistula creation); systolic pressure after fistula creation; systolic pressure change after fistula creation (e.g. as compared to systolic pressure prior to fistula creation); ratio of diastolic to systolic pressure after fistula creation; difference between diastolic pressure and systolic pressure after fistula creation; and combinations of these.

Fistula modification procedures can include but are not limited to: increasing flow through the fistula; decreasing flow through the fistula; increasing the diameter of at least a segment of the fistula; decreasing the diameter of at least a segment of the fistula; removing tissue proximate the fistula; blocking a sidebranch proximate the fistula; and combinations of these. A fistula modifying device can include one or more devices selected from the group consisting of: an over the wire device constructed and arranged to be delivered over a vessel-to-vessel guidewire as described herein; an expanding scaffold configured to increase or otherwise modify fistula geometry such as an expandable balloon; an energy delivery catheter such as a catheter configured to deliver energy to tissue proximate a fistula; an agent delivery catheter such as a catheter configured to deliver an agent such as a pharmaceutical agent or an adhesive such as fibrin glue; and combinations of these.

In some embodiments, a second fistula is created, such as using the techniques of STEP 20 described hereabove. The second fistula can be created in the same clinical procedure as STEP 20 (in which the first fistula is created), or in a subsequent clinical procedure such as a procedure performed at least twenty-four hours after completion of STEP 20, or at least 1 week, at least 1 month, and/or at least 6 months after completion of STEP 20. A second fistula can be created due to inadequate therapy provided by the first fistula, and/or if the first fistula has insufficient flow (e.g. becomes non-patent). A second fistula can be created due to formation of a vascular (e.g. venous) stenosis proximate the first fistula. In these embodiments, the first fistula can be reversed (e.g. closed), such as through the placement of a covered stent graft in the vein or artery that covers the fistula, or other fistula-occlusive procedure.

The method of FIG. 1 can be performed using real-time imaging, such as real-time imaging provided by a fluoroscope and/or an ultrasound imaging device.

The method of FIG. 1 can be performed to decrease peripheral vascular resistance, such as to decrease infrarenal vascular resistance (e.g. below the kidneys or in a manner to include the great vessels of the aorta and/or the inferior vena cava). Alternatively or additionally, the method can be performed to achieve a physiologic change selected from the group consisting of: increased oxygen delivery by the arterial system; increased blood volume; increased proportion of blood flow to the descending aorta; increased blood flow to the kidneys; increased blood flow outside the kidneys; increased cardiac output; and combinations of these. The method can be constructed and arranged to prevent any significant chronic increase in heart rate. Alternatively or additionally, the method can be constructed and arranged to prevent a decrease in cardiac function. Alternatively or additionally, the method can be constructed and arranged to avoid undesired adverse effects to the kidneys, such as by avoiding the adverse effects that can be encountered in a renal denervation procedure, such as stenosis, lost autonomic control and/or vessel intima damage.

In some embodiments, the method is performed to increase oxygenation and/or flow rates associated with the patient's chemo-receptors, such as to cause a therapeutic change to vascular resistance. In some embodiments, the method is performed to affect or otherwise modify the patient's central sympathetic tone. Modifications to central sympathetic tone can be performed to reduce systolic and/or diastolic blood pressure (e.g. mean systolic and/or mean diastolic blood pressure), and/or to treat other patient diseases and conditions such as diabetes, sleep apnea, or heart failure.

In some embodiments, the method of FIG. 1 is constructed and arranged to cause a reduction in diastolic blood pressure that is equal to or greater than a concurrent reduction in systolic blood pressure, such as are presented in Table 3 described hereinbelow. In some embodiments, the method is constructed and arranged to reduce the diastolic pressure more than the systolic pressure by an amount of at least 2 mmHg, at least 4 mmHg or approximately 5 mmHg. In some embodiments, the method is constructed and arranged to reduce the diastolic pressure by at least 5 mmHg, such as a reduction of at least 10 mmHg, at least 15 mmHg or approximately 18 mmHg. In some embodiments, the method is constructed and arranged to reduce the systolic pressure by at least 5 mmHg, such as a reduction of at least 10 mmHg or approximately 13 mmHg. In some embodiments, the method is constructed and arranged to cause a reduction in blood pressure to a level at or below 130/90 mmHg.

The method of FIG. 1 and associated clinical testing has been performed by applicant in a study in patients with hypertension and COPD. In the study, the patients with hypertension received a significant and beneficial drop in blood pressure as a result of the fistula creation. Twenty four of the patients studied had systolic pressure greater than 130 mmHg. In each patient, a 4 mm fistula was created to shunt blood from the right iliac artery to the right iliac vein. Cardiac output was measured before and after the procedure, and blood pressure was recorded before the procedure and again at 3, 6, 9 and 12 months. The creation of a fistula in the iliac region increased cardiac outputs by 41% ($p<0.01$), with a mean percentage change of 44%. An unexpected outcome was that patients with high blood pressure soon had a substantial drop in both their systolic and diastolic blood pressures. In previously performed large population studies, a 10 mmHg drop in systolic blood pressure has been associated with a 40% reduction in risk of stroke mortality and a 30% reduction in risk of death due to coronary disease. A year after the procedure, average drop in systolic blood pressure was 13 mmHg lower (SD 17; $p<0.01$) and the average drop in diastolic blood pressure was 18.4 mmHg (SD 12; $p<0.0001$). The only significant adverse effect of the procedure was the development of venous stenosis in the iliac vein above the site of the fistula. This adverse event occurred in four subjects, but was corrected by placing a covered stent in the iliac vein over the fistula. Detailed information on the study is provided immediately herebelow.

Methods & Participating Patients

Patients were selected based on several inclusion and exclusion criteria, including the ability to undergo arteriovenous fistula creation, GOLD Stage II or greater COPD, and participants were without a current exacerbation of COPD and were on stable medication for a minimum of 4 weeks prior to enrollment. The criteria for exclusion included pulmonary arterial hypertension (a mean Pulmonary Arterial Pressure greater than 35 mmHg), obesity (Body Mass Index greater than 31 kg·m-2 male or 32 kg·m-2 female), liver cirrhosis, recent stroke or heart failure (within 6 months), unstable coronary artery disease, and malignant cancer that might adversely affect the subject's safety. A large group of patients (n=67) had an arteriovenous fistula created as part of a multi-center international study of arteriovenous fistula creation in patients with severe COPD. In addition to parameters concerned with exercise capacity and pulmonary function, subjects were also evaluated for office-based blood pressure and hemodynamic measures during cardiac catheterization at baseline and follow-up. Of particular note were twenty-four subjects with high blood pressure (subjects who, in spite of anti-hypertensive therapy had systolic blood pressure recordings greater than 130 mmHg at baseline) who were not known to have a secondary cause of hypertension. Blood pressure and hemodynamic changes in those twenty-four hypertensive subjects are reported herein. Patients underwent percutaneous arteriovenous fistula creation using an anastomotic clip such as anastomotic clip 160 of FIG. 2 described hereinbelow. Assessment included physical examination, clinic based blood pressure recordings, and cardiac catheterization to measure cardiac output, oxygen delivery, and both pulmonary and systemic vascular resistances.

Procedure

In each procedure, an anastomotic clip was deployed in the iliac region to create an iliac arteriovenous fistula. Vascular femoral venous and arterial access was obtained using standard interventional techniques. FIGS. 3A and 3B illustrate the 7 French anastomotic clip delivery device used, including the anastomotic clip which was implanted. In some embodiments, the anastomotic clip delivery device comprises device 150, and the anastomotic clip comprises device 160, each of FIG. 2 herebelow. In FIG. 3C, an angiogram of the iliac artery A and iliac vein V prior to shunt creation is illustrated. A vessel targeting wire CW, such as wire 120 of FIG. 2, outlines the iliac artery, and a venogram confirms vessel proximity and target crossing location for the creation of the arteriovenous fistula. A 22 gauge crossing needle, such as a needle of deployment device 140 of FIG. 2 herebelow, is placed into the vein over a guidewire and through an 11 French introducer device, not shown but such as introducer 110 also of FIG. 2 herebelow. The 22 gauge crossing needle has been advanced through the wall of the iliac vein into the iliac artery, and a guidewire advanced through a lumen of the needle and into the artery. In the procedure, the needle was subsequently removed and the anastomotic clip delivery system tracked across the puncture site. The anastomotic clip was then deployed so that the expanded arms of the anastomotic clip attached to the inner walls of the iliac artery and iliac vein, and the retention arms maintained the anastomotic clip in the proper position (deployed position shown in FIG. 3D). After removal of the delivery system, a 4-mm balloon catheter was inserted into the center of the anastomotic clip and inflated to expand the anastomotic clip to a 4-mm diameter. The balloon was then deflated and removed. An angiogram confirmed the patency of the fistula. Subjects were prescribed aspirin and compression stockings after the procedure.

Baseline measurements consisted of vital signs, physical examination and cardiac catheterization. Follow-up assessments were performed at 3, 6, 9, and 12 months, which consisted of office blood-pressure measurement, physical examination, and surveillance for adverse events. Blood pressures were recorded in an office setting and in accordance with standard Joint National Committee VII guidelines. Subjects also underwent repeat cardiac catheterization 3 to 6 months after the creation of the fistula. Cardiac output was measured in all but five subjects using a thermodilution catheter technique. In five subjects the baseline and follow-up cardiac output were measured using the Fick technique.

Statistical Analysis

All blood pressure analyses were performed post-hoc. Changes in office-based blood pressure were analyzed over 12 months of follow-up and compared with baseline blood pressure by repeated measures analysis of variance with pair-wise comparison of significant values. To assess the hemodynamic effect of arteriovenous fistula creation, hemodynamic measures were compared between baseline and repeat cardiac catheterization (between 3 and 6 months after the creation of the fistula) using paired t-tests. Adverse events were also recorded. A p value of less than 0.05 was regarded as statistically significant. Multiple linear regression analysis was performed to determine whether an association exists between changes in hemodynamic measures and changes in office based blood pressure and age, gender, baseline heart rate, and baseline severity of COPD.

Results—Characteristics of the Patients:

While testing the creation of an iliac arteriovenous fistula using a percutaneously deployed nitinol anastomotic clip in sixty-seven patients with COPD, twenty-four (13 male) subjects were included who had both a systolic blood pressure greater than 130 mmHg and severe COPD (mean post-bronchodilator FEV1=30% predicted). The procedure was successful in all cases. Their demographic details are contained in Table 1. Two thirds of patients (n=16) had a systolic blood pressure greater than 140 mmHg at baseline, while 21% had a systolic blood pressure greater than 160 mmHg There was no gender or race/ethnic based difference in outcome. Arterial blood pressure at enrollment was 145/86 mmHg (SD 12/13), with a heart rate of 91 beats per minute (SD 16). Patients took, on average, 2 anti-hypertensive medications, with (29%) receiving an angiotensin-converting enzyme inhibitor, (17%) an angiotensin II receptor blocker, (17%) beta-blockers, (25%) calcium-channel blockers, and (8%) direct vasodilators. Almost half (46%) of the hypertensive patients also took diuretics as shown in Table 1 immediately herebelow.

TABLE 1

Baseline demographics of the 24 subjects with severe COPD and hypertension who underwent creation of the arteriovenous fistula. Data are presented as mean (standard deviation).

| | |
|---|---|
| Number of subjects | 24 |
| Age years | 65 (6) |
| Male gender | 54% |
| Body mass index kg · m$^{-2}$ | 25 (5) |
| Cigarette consumption (pack years) | 47 (25) |
| Systolic blood pressure mmHg | 145 (12) |
| Diastolic blood pressure mmHg | 86 (13) |
| Mean arterial blood pressure mmHg | 105 (12) |
| Serum creatinine mg/dl | 0.84 (.26) |
| Diuretic | 46% |
| ACE inhibitor | 29% |
| Angiotensin receptor blocker | 17% |
| Beta-blocker | 17% |
| Vasodilator (nitrate) | 8% |
| Calcium channel blocker | 25% |
| Post-bronchodilator FVC (% predicted) | 68 (22) |
| Post-bronchodilator FEV$_1$ (% predicted) | 30 (11) |
| PaO$_2$ mmHg on Room air | 63 (9) |
| PaCO$_2$ mmHg on Room air | 42 (6) |

Results—Blood Pressure Lowering Effect:

The average blood pressure measurements were: 145/86 mmHg, 139/76 mmHg, 130/71 mmHg, 132/74 mmHg, and 132/67 mmHg at baseline, 3 months, 6 months, 9 months, and 12 months respectively, as shown in FIGS. 3E and 3F. By the end of the study period (12 months) the systolic blood pressure was reduced from 145 (SD 12) mmHg to 132 (SD 18) mmHg (p<0.01) and the diastolic blood pressure was reduced from 86 (SD 13) mmHg to 67 (SD 13) mmHg (p<0.0001). Multiple comparison testing revealed significant differences in systolic blood pressure between baseline and 3 months, baseline and 6 months, baseline and 9 months, and baseline and 12 months and a significant difference was also seen between 3 months and 12 months, as shown in FIG. 3E and FIG. 4. Multiple comparison testing revealed significant differences in diastolic blood pressure between baseline and 6 months, baseline and 9 months, and baseline and 12 months, as is shown in FIG. 3F and FIG. 4. Multivariable analysis showed a significant association between baseline diastolic blood pressure and changes in diastolic pressure at 12 months (p<0.02) but failed to show a clear association between blood-pressure reduction and any of the following: age, gender, baseline heart rate, baseline severity of COPD (PaO2 and FEV1). At baseline, patients were taking an average of two anti-hypertensive medications, which did not change during follow-up.

Results—Hemodynamic Changes Assessed During Cardiac Catheterization:

Cardiac catheterization revealed increases in cardiac output (from 6 (SD 2) liters/min at baseline to 8.4 (SD 3) liters/min, p<0.001) and oxygen delivery (from 1091 (SD 432) ml/min to 1441 (SD 518) ml/min, p<0.001), accompanied by reductions in mean arterial pressure (106 (SD 12) mmHg to 97 (SD 12) mmHg, p<0.001), systemic vascular resistance (1457 (SD 483) dynes to 930 (SD 335) dynes, p<0.001), and pulmonary vascular resistance (190 (SD 117) dynes to 140 (SD 77) dynes, p<0.01). Although no change was detected in the right atrial pressures and heart rates, there were small but significant increases in both the pulmonary arterial pressure (25 (SD 5) mmHg at baseline to 29 (SD 6) mmHg at follow-up, p<0.01), and the pulmonary capillary wedge pressure (12.2 (SD 5) mmHg at baseline to 15.5 (SD 7) mmHg at follow-up, p=0.01). Multivariable regression revealed an association between changes in cardiac output and changes in pulmonary vascular resistance (p<0.05) and between changes in cardiac output and changes in systemic vascular resistance (p<0.05). Changes in pulmonary capillary wedge pressure (PCWP) were associated with changes in systemic vascular resistance (p<0.05) but were not associated with changes in pulmonary vascular resistance (PVR).

The median procedure time (from skin to skin) was 53 minutes (range 20 minutes to 2 hours and 15 minutes). Among the twenty-four patients who underwent arteriovenous fistula creation, the procedure was completed without complication in twenty of the patients. Within 7 days of the procedure, two patients developed pseudoaneurysm at the femoral access site, which was successfully treated with manual compression; one patient developed mild chest pressure and chest pain, which resolved; and one patient developed a clot around the fistula which resolved after anti-coagulant therapy. Late adverse events included four patients who developed deep venous thrombosis (resolved with anti-coagulation) and another patient in whom the shunt was closed in a separate clinical procedure (at 11 months), because of a lack of clinical improvement. Four subjects developed a venous stenosis of the iliac vein cephalad to the device. Two of these cases were initially treated with dilatation, however the stenosis recurred, and they were then successfully treated with stent placement. The other pair was successfully treated with stent placement without recurrence. In one case, the stent was undersized, resulting in dislodgement and migration into the right ventricle. The stent was retrieved and repositioned in the left iliac vein with no sequelae, and the venous stenosis was successfully treated with an appropriately sized self-expanding stent. There was no death during the 12-month follow-up period. In patients whose baseline creatinine level was higher than 1.0 mg/dl (n=4, average creatinine was 1.29 mg/dl, range 1.05 to 1.51 mg/dl), there was a significant increase in glomerular filtration rate, eGFR (MDRD). Their eGFR at 12 months was increased to 67 (SD 18) ml/min from 54 (SD 18) ml/min at baseline, (p=0.02).

DISCUSSION

The study provides significant data demonstrating the efficacy of the methods, systems and devices of the present inventive concepts to treat hypertension. Patients suffering from arterial hypertension that received a peripheral arteriovenous fistula had a significant reduction in their blood pressure. A year after the procedure, their systolic blood pressures are an average of 13 mmHg lower, and their diastolic pressures are an average of 18 mmHg lower. In fact, the higher the diastolic pressure before the procedure, the greater is the drop in diastolic pressure. The number of patients with hypertension (a systolic blood pressure greater than 140 mmHg) is halved (16 to 8).

The methods, systems and device of the present inventive concepts provide a painless percutaneous procedure producing rapid reductions in blood pressure. Deployment of the device employs iliofemoral vascular access with a catheter guidance system, and (through a series of crossing needles and dilators) creation of a 4 mm fistula between the iliac artery and iliac vein. The fistulas remained patent (100% patency rate at 1 year) and is remarkably well tolerated, even in these elderly patients with advanced lung disease.

Blood pressure lowering effect is not the only hemodynamic effect of this procedure. Our hemodynamic data obtained via cardiac catheterization correlate to increased cardiac output and oxygen delivery, and the study results demonstrated significant reductions in pulmonary vascular resistance and systemic vascular resistance. The drop in pulmonary vascular resistance appears to be associated with changes in cardiac output, rather than increases in pulmonary capillary wedge pressure or increases in mixed venous oxygen content (see Table 2 herebelow). This drop in pulmonary vascular resistance is supported by applicant's work on pulmonary hypertensive disease in rats, which showed that the creation of a modest arteriovenous shunt attenuates rather than accelerates the development of pulmonary vascular disease.

TABLE 2

Hemodynamic values at baseline and on repeat cardiac catheterization post insertion of the arteriovenous anastomotic clip (n = 23).

|  | Baseline | Repeat* | p value |
|---|---|---|---|
| Heart rate (bpm) | 91 (16) | 92 (16) | 0.85 |
| Mean arterial pressure mmHg | 106 (12) | 97 (12) | 0.001 |
| Right atrial pressure mmHg | 8 (4) | 9.5 (4) | 0.17 |
| Cardiac output (liters/min) | 6 (2) | 8.4 (3) | <0.001 |
| Oxygen delivery (ml. min.$^{-1}$) | 1091 (432) | 1441 (518) | <0.001 |
| Systemic vascular resistance dynes | 1457 (483) | 930 (335) | <0.001 |
| Mean pulmonary arterial pressure mmHg | 25 (5) | 29 (6) | <0.01 |
| Mixed venous oxygen saturation % | 73 (6) | 79 (5) | <0.001 |
| Pulmonary capillary wedge pressure mmHg | 12.2 (5) | 15.5 (7) | 0.01 |
| Pulmonary vascular resistance dynes | 190 (117) | 140 (77) | <0.01 |

*Repeat cardiac catheterization was performed between 3 and 6 months after creation of an arteriovenous fistula.

Table 3 herebelow represents ambulatory blood pressure data for eight patients who received the fistula creation procedure of the present inventive concepts. The data includes daytime and nighttime blood pressures for each patient at baseline and 1 month, 3 months and 6 months after the fistula creation procedure. Patient 1 and Patient 3 daytime blood pressure significantly decreased at nighttime over six months as compared with baseline blood pressure. Patient 2 is a diabetic on multiple medications and saw a significant decrease in daytime blood pressure by six months. Patient 4 received Tegretol (carbamaepine) and Lipitor (atorvastatin) between baseline and three months. Patient 5 is resistant to all hypertension medications. Patient 6 nighttime blood pressure significantly decreased at three months such that the patient's blood pressure decreased from daytime to nighttime. Patient 7 diastolic blood pressure significantly dropped in the daytime and nighttime by 1 month. Patient 8 systolic blood pressure entered normal range in the daytime and nighttime at 1 month.

TABLE 3

Ambulatory Blood Pressure (BP) Daytime/Nighttime Changes for 8 Patients

| Patient | Baseline Day | Baseline Night | 1 Mo Day | 1 Mo Night | 3 Mo Day | 3 Mo Night | 6 Mo Day | 6 Mo Night |
|---|---|---|---|---|---|---|---|---|
| 1 | 162/98 | 150/90 | 159/78 | 132/60 | 158/80 | 140/69 | 160/75 | 135/60 |
| 2 | 159/72 | 126/64 | 158/67 | 134/59 | 135/55 | 126/53 | 133/57 | 124/53 |
| 3 | 152/86 | 138/73 | 151/76 | 133/64 | 144/77 | 127/63 | 143/71 | 127/61 |
| 4 | 163/76 | 147/72 | 148/65 | 139/62 | 158/71 | 154/68 | — | — |
| 5 | 189/113 | 181/108 | 197/103 | 166/88 | 192/110 | 182/99 | — | — |
| 6 | 135/69 | 131/62 | 129/59 | 125/61 | 138/69 | 119/60 | — | — |
| 7 | 143/86 | 149/89 | 145/71 | 146/74 | — | — | — | — |
| 8 | 140/74 | 133/68 | 127/60 | 126/61 | — | — | — | — |

Table 4 herebelow represents average serum creatinine data for three patients who received the fistula creation procedure of the present inventive concepts. The data includes serum creatinine levels for three patients having Stage II Hypertension and elevated serum creatinine levels for four patients at baseline at baseline and three months, six months, nine months, and twelve months after the fistula creation procedure. The data indicates a sustained decrease in serum creatinine levels representative of increased kidney perfusion, thus improved renal function. The analysis showed no correlation between change in serum creatinine and weight over the course of the twelve months follow up.

TABLE 4

Average serum creatinine levels for 3 Patients representative of increased kidney perfusion and improved renal function

| | Baseline | 3 Mo | 6 Mo | 9 Mo | 12 Mo |
|---|---|---|---|---|---|
| Serum Creatinine Levels (mg/dL) Stage II Hypertension | 1.10 | 0.96 | 0.95 | 0.85 | 0.90 |
| Serum Creatinine Levels (mg/dL) Elevated Levels at Baseline | 1.29 | 1.30 | 1.10 | 1.00 | 1.04 |

Table 5 herebelow represents the results from an evaluation of cardiac function for patients who received the fistula creation procedure of the present inventive concepts. Echocardiogram results demonstrated no change, and in some cases, an improvement to cardiac function for those patients receiving the fistula creation procedure. Control data indicated a decline in cardiac function for some patients.

TABLE 5

Change in Cardiac Function: Data represented by # of patients/total # of patients

| | ROX Device | | Control | |
|---|---|---|---|---|
| | 6 Month | 12 Month | 6 Month | 12 Month |
| No Change | 15/19 | 11/15 | 13/20 | 11/16 |
| Improvement | 4/19 | 3/15 | 3/20 | 1/16 |
| Decline | 0/19 | 1/15 | 4/20 | 4/16 |

Figure 2:
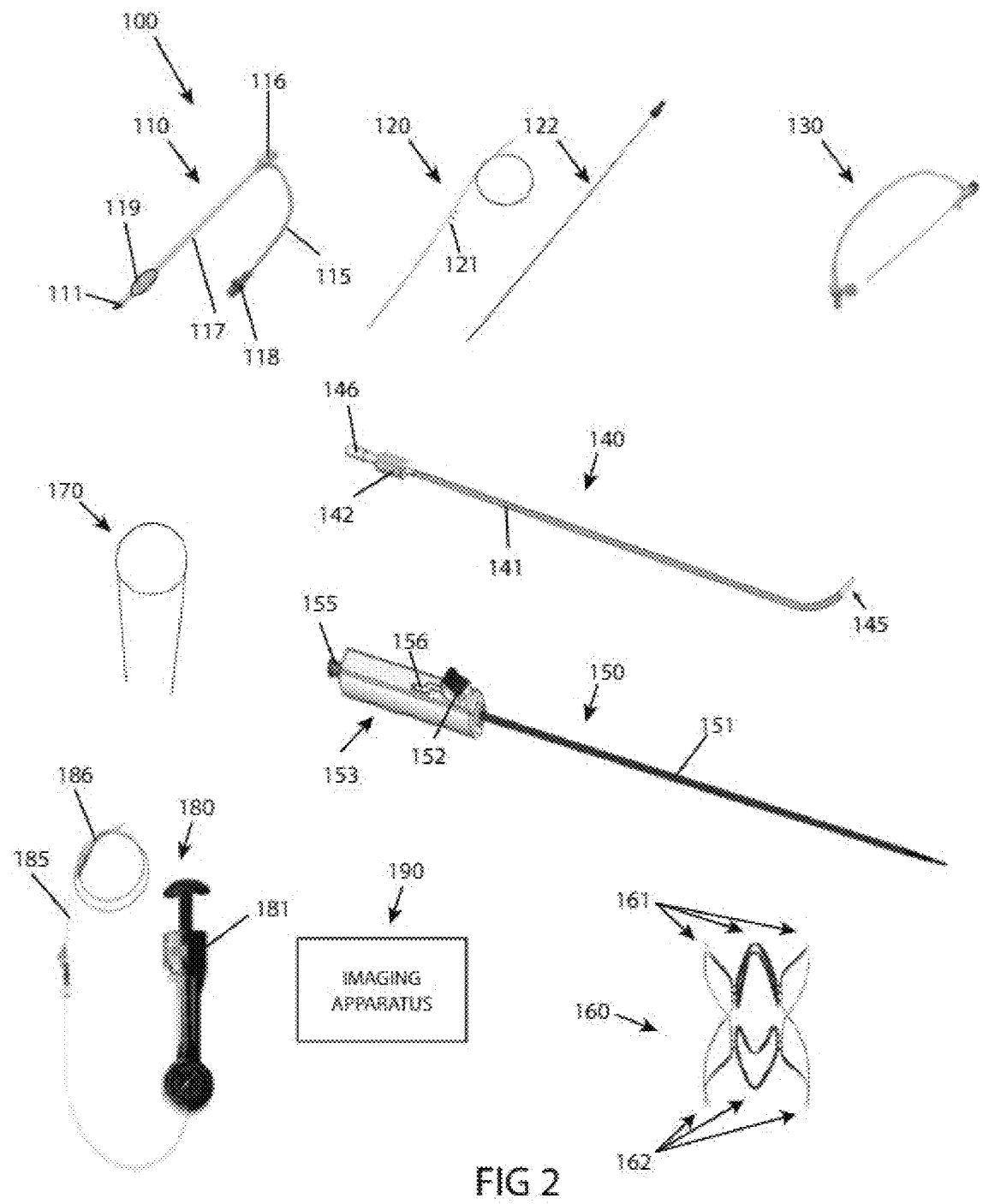
FIG. 2 is a schematic view of a system for creating a flow pathway in a patient, consistent with the present inventive concepts.
Figure 3A:
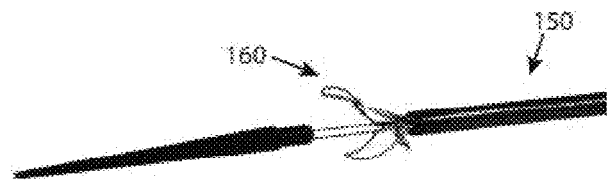
FIGS. 3A through 3D are a set of steps for implanting an anastomotic clip, consistent with the present inventive concepts.
Figure 3B:
Figure 3C:
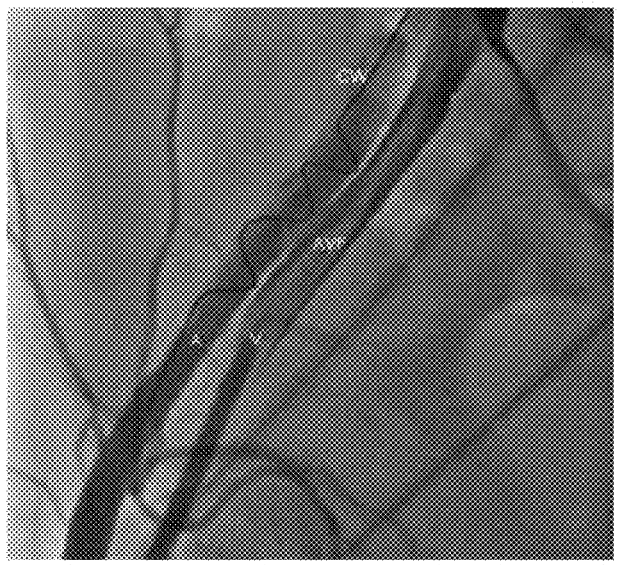
Figure 3D:
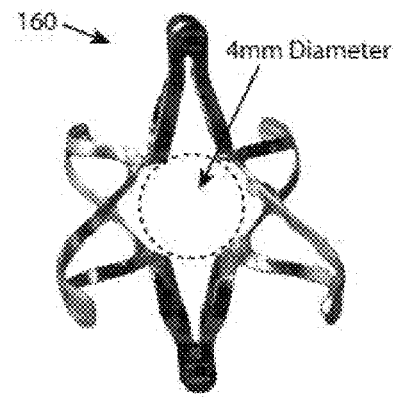

Referring now to FIG. 2, a system for creating a fistula or other flow pathway between a first location in a patient's arterial system of a patient (e.g. an artery), and a second location in the patient's venous system (e.g. a vein), is illustrated. System 100 comprises a vascular introducer, first introducer 110, configured to be placed into the patient to provide access to a starting vessel. System 100 comprises another vascular introducer, second introducer 130, configured to provide access to a target vessel. In some embodiments, the starting vessel is a vein, and the target vessel is an artery. In other embodiments, the starting vessel is an artery and the target vessel is a vein. System 100 can include target wire 120 which comprises helical section 121 and is configured to be placed through the second introducer 130 and into the target vessel. Target wire 120 can be placed through an elongate tube, catheter 122. System 100 can comprise needle deployment device 140 which is configured to deploy crossing needle 145 (shown in an advanced position in FIG. 2), from the starting vessel and into the target vessel. System 100 can include a vessel-to-vessel guidewire 170, which can be placed from the starting vessel to the target vessel via needle deployment device 140. System 100 can also include clip deployment catheter 150, which is configured to deploy anastomotic clip 160. System 100 can include a fistula modifying device, such as dilation device 180 including balloon catheter 185 and standard angioplasty balloon indeflator 181. System 100 can further comprise imaging apparatus 190, typically a fluoroscope and/or ultrasound imaging device used to image one or more device or components of system 100, as well as the patient's anatomy, during the creation of an arteriovenous fistula.

First introducer 110 is configured to be placed into the patient to provide access to a starting vessel (e.g. a vein of a patient). In some embodiments, introducer 110 comprises an 11 French vascular introducer. First introducer 110 can comprise beveled tip 111 with an angle ranging from 20° to 50°, such as at an angle of approximately 30°. Additionally, system 100 can include a kit comprising an additional introducer having a second angle providing the clinician or other user (hereinafter "clinician) with more options as may be appropriate for a particular patient's anatomical geometry. In some embodiments, beveled tip 111 comprises a marker, for example, a radiopaque or other visualizable marker, such that the luminal wall of the starting vessel can be imaged (e.g. when tip 111 is pressed against the vessel wall). The proximal portion of introducer 110 can comprise a contour or marker, such as to be correlated with or otherwise indicate the alignment of the bevel of tip 111.

Introducer 110 comprises shaft 117 which includes at least one thru lumen. Introducer 110 also comprises port 116, typically a hemostasis valve, which is fluidly connected to the lumen of shaft 117. A second port 118, typically a luer connector, is connected to tubing 115 which in turn is connected to port 116. Introducer 110 can further comprise a dilator, not shown but typically an 11 to 13 French dilator used to introduce and/or pre-dilate tissue receiving introducer 110. Introducer 110 can further comprise a radially expandable element, such as expandable element 119, such as a balloon or expandable cage located on its distal portion. In some embodiments, expandable element 119 can be configured to prevent advancement of introducer 110 into the target vessel. In yet another embodiment, expandable element 119 can be configured to stabilize the starting vessel during insertion of introducer 110 or another device or component of system 100.

System 100 can comprise second introducer 130 which is configured to provide access to a target vessel, such as an artery of the patient when the starting vessel is a vein. In some embodiments, second introducer 130 comprises a 4 French vascular introducer. System 100 comprises target wire 120 configured to be placed through second introducer 130 and into the target vessel. Target wire 120 can comprise helical section 121 configured to be deployed at the site where the fistula is to be created. Helical section 121 can be configured to provide structure and support to the site during a procedure. Additionally, target wire 120 can serve as a visual reference during insertion of vessel-to-vessel guidewire 170, as described herebelow.

System 100 can comprise needle deployment device 140. Needle deployment device 140 comprises shaft 141 which slidingly receives advanceable crossing needle 145, shown in an advanced state. Shaft 141 comprises shaft hub 142 mounted to its proximal end. Shaft 141 can comprise a curved distal portion as shown. Crossing needle 145 comprises needle hub 146 mounted to its distal end. Movement of needle hub 146 relative to shaft hub 142 causes crossing needle 145 to advance and retract within shaft 141. Needle hub 146 is fully advanced toward shaft hub 142 in the configuration of FIG. 2, such that the tip and distal portion of crossing needle 145 is fully advanced out of the distal end of shaft 141.

Crossing needle 145 can comprise a 20 to 24 gauge needle, such as a 22 gauge needle. In some embodiments, the crossing needle comprises a curved distal portion (as shown). The curved distal portions of shaft 141 and/or needle 145 can be aimed at the center of the target vessel prior to insertion into the target vessel. The radius of curvature can be reduced if the clinician has difficulty in aiming the needle tip at the center of the target vessel prior to insertion. Conversely, the radius of curvature can be increased to sufficiently aim the needle tip at the center of the target vessel. Additionally, the crossing needle 145 can comprise a marker, not shown but indicating the direction of curvature. Examples of markers include, but are not limited to: a flat surface, a textured surface; a visualizable marker such as a radiopaque marker, a magnetic marker, an ultrasonic marker or a visible marker; and combinations of these. In some embodiments, crossing needle can comprise a shaped memory alloy, for example, nickel titanium alloy. In some embodiments, shaft hub 142 and/or needle hub 146 comprise a marker or other visible demarcation (e.g. a flat portion) which correlates to the direction of curvature of shaft 141 and/or crossing needle 145, respectively.

System 100 can comprise a guidewire to be placed from the starting vessel to the target vessel, vessel-to-vessel guidewire 170. Guidewire 170 is configured to be placed via needle deployment device 140. In some embodiments, vessel-to-vessel guidewire 170 comprises a wire with an outer diameter of approximately 0.018". Vessel-to-vessel guidewire 170 can comprise a marker, not shown but configured to indicate the fistula location. In some embodiments, vessel-to-vessel guidewire 170 comprises a distal portion and a mid portion. Guidewire 170 mid portion can comprise a different construction than the distal portion. For example, the mid portion of guidewire 170 can be stiffer than the distal portion.

System 100 can comprise clip deployment catheter 150 configured to house and deploy anastomotic clip 160. Clip 160 comprises a plurality of distal arms 161 and a plurality of proximal arms 162, which can be deployed simultaneously or independently. Clip 160 comprises at least two distal arms 161 and at least two proximal arms 162 configured to deploy and engage the starting vessel and the target vessel. In some embodiments, clip 160 comprises four deployable distal arms 161 and four deployable proximal arms 162. Clip 160 can comprise a shaped memory alloy, such as nickel titanium alloy. In some embodiments, clip 160 is constructed and arranged as described in applicant's U.S. Pat. No. 7,828,814, entitled "Device and Method for Establishing an Artificial Arterio-Venous Fistula", filed Apr. 4, 2007, the contents of which are incorporated herein by reference in its entirety.

In some embodiments, clip 160 is biodegradable or includes one or more biodegradable portions (e.g. one or more portions of clip are absorbed or otherwise degrade over time). In some embodiments, clip 160 comprises a biodegradable anastomotic device such as is described in applicant's co-pending U.S. Non-Provisional application Ser. No. 12/752,397, entitled "Device and Method for Establishing an Artificial Arteriovenous Fistula", filed Apr. 1, 2010, the contents of which are incorporated herein by reference in its entirety.

Clip deployment catheter 150 comprises shaft 151. Mounted to the proximal end of shaft 151 is handle 153. On the proximal end of handle 153 is port 155, which is operably attached to shaft 151 such that a guidewire can travel from the distal end of shaft 151 to port 155, such as guidewire 170 after it has been previously placed between a starting vessel and a target vessel as has been described hereabove. Shaft 151 comprises one or more tubular portions, such as an inner tubular segment that houses clip 160, and an outer tubular segment that covers clip 160 but can be retracted to deploy clip 160, such as is described in applicant's co-pending U.S. Non-Provisional application Ser. No. 11/152,621, entitled "Devices for Arterio-Venous Fistula Creation", filed Jun. 13, 2005, the contents of which is incorporated herein by reference in its entirety. The clip deployment catheter 150 and the anastomotic clip 160 to be delivered may be similar to the clip deployment apparatus 200 and clip 250, respectively, described below.

Handle 153 further includes control 152 (e.g. a button, slide or lever), where control 152 is operably configured to allow an operator to deploy distal arms 161 and/or proximal arms 162 of clip 160, such as via retraction of an outer tube or sheath portion of shaft 151 that is covering one or more portions of clip 160. In some embodiments, a click or other tactile feedback is provided during retraction of a sheath portion of shaft 151. Control 152 can be moved via a stepped or otherwise segmented slot 156. Distal arms 161 can be deployed via moving control 152 from a "first ready to deploy" position to a "first deployed" position which can be achieved by moving control 152 relatively parallel to the longitudinal axis of handle 153. The at least two proximal arms 162 can be queued to be deployed via moving control 152 from the first deployed position to a "second ready to deploy" position. The second ready to deploy position can be achieved by moving control 152 in a direction perpendicular to the longitudinal axis of the handle. Subsequently, proximal arms 162 can deployed via moving control 152 from the second ready to be deployed position to a "second deployed" position via a motion parallel to the longitudinal axis of the handle. In this embodiment, control 152 can include a safety position comprising a ready to deploy position which can be transitioned by moving control 152 in a direction that is perpendicular to the axis of handle 153. This control advancement arrangement can prevent inadvertent deployment of distal arms 161 and/or proximal arms 162.

In some embodiments, prior to deployment of one or more arms of clip 160, introducer 110 can be advanced such that end 111 applies a force to the wall of the starting vessel. Sufficient force can be applied by introducer 110 to enable an operator to "seat" the starting vessel against the target vessel to assist in properly deployment of clip 160.

In some embodiments, catheter 150 can be configured to recapture distal arms 161 and/or proximal arms 162. For example, clip deployment catheter 150 can deploy at least one distal arm 161 and subsequently recapture the at least one distal arm 161.

Clip deployment catheter 150 and/or clip 160 can further comprise at least one marker, not shown but typically a radiopaque and/or ultrasonic marker configured to assist in the rotational positioning of clip 160 at the fistula location. For example, the marker can be oriented toward the target vessel prior to deployment of clip 160. In some embodiments, a marker is included on the distal portion of clip deployment catheter 150. In some embodiments, handle 153 comprises one or more markers that are circumferentially aligned with clip 160 prior to its deployment. In some embodiments, clip deployment catheter 150 and/or clip 160 comprise at least one marker configured to longitudinally position clip 160 at the fistula location. In these embodiments, the marker can indicate the distal and/or proximal end of clip 160.

Clip deployment catheter 150 can further comprise a projection and/or recess, neither shown but configured to mechanically engage clip 160. The project and/or pin can be used to stabilize clip 160 with shaft 151, such as when an outer tubular portion of shaft 151 is advanced or retracted.

System 100 can comprise dilation device 180 configured to dilate clip 160 and/or the fistula. Dilation device 180 can include balloon catheter 185, such as a standard angioplasty balloon catheter comprising balloon 186. Attached to the proximal end of catheter 185 is indeflator 181, typically a standard balloon indeflator device. Alternatively, balloon 186 can comprise a non-balloon expandable such as an expandable cage or radially deployable arms configured to dilate the fistula. Catheter 185 is configured to track over a vessel-to-vessel guidewire, such as guidewire 170 placed between a vein and an artery, such that balloon 186 is positioned within the fistula (e.g. within clip 160). Typically, dilation device 180 can expand to a diameter of less than five millimeters, and more typically to a diameter of approximately four millimeters. In some embodiments, a second dilation device 180 is included, such as a device configured to expand to a different diameter than the first dilation device.

System 100 can include patient imaging apparatus 190. Non-limiting examples of an imaging apparatus include: x-ray; fluoroscope; ultrasound imager; MRI; and combinations of these. The imaging apparatus can allow the clinician to track the movement of all components comprising system 100 as well as view the position of the starting and target vessel relative to each other, as described in detail herein.

Figure 5:
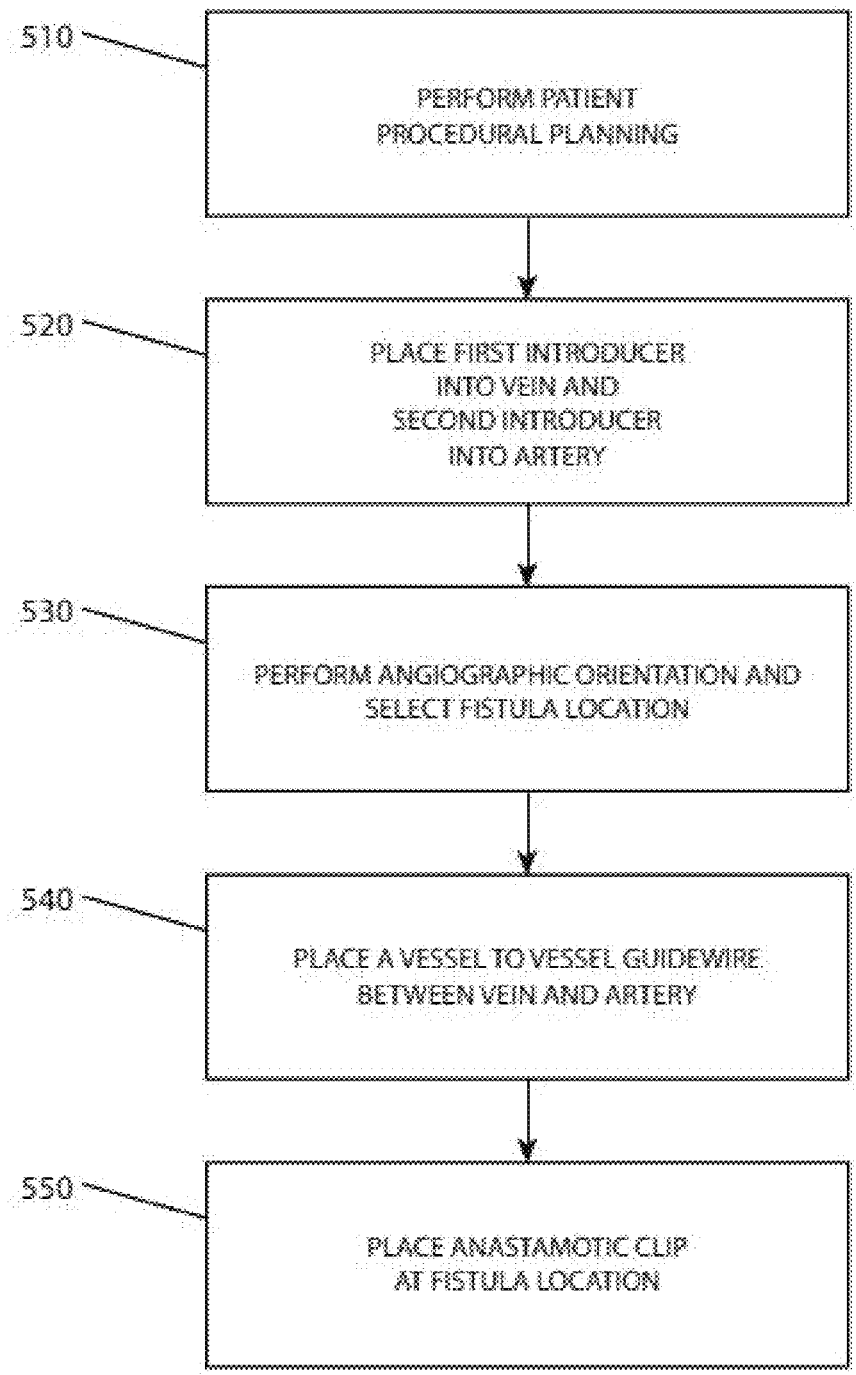
FIG. 5 is a flow chart of a method for treating a patient with a flow pathway, consistent with the present inventive concepts.

Referring now to FIG. 5, a flow chart of a method of creating a fistula between a starting vessel and a target vessel at a fistula location, consistent with the present inventive concepts is illustrated. In Step 510, a procedural planning assessment of a patient is performed. Step 520 comprises placing a first introducer into a starting vessel, e.g. a vein, and placing a second introducer into a target vessel, e.g. an artery. In Step 530, an angiographic orientation is performed and a fistula location is selected. Step 540 comprises placing a vessel-to-vessel guidewire between the vein and the artery. Step 550 comprises placing an anastomotic clip at the fistula location. In some embodiments, system 100 and/or one or more components of system 100 of FIG. 2 are used to perform the method of FIG. 5.

The starting vessel can comprise a vein, and can be selected from the group consisting of: inferior vena cava (IVC); saphenous; femoral; iliac; popliteal; brachial; basilic; cephalic; medial forearm; medial cubital; axillary; and jugular. The target vessel can comprise an artery, and can be selected from the group consisting of: aorta; axillary; brachial; ulnar; radial; profundal; femoral; iliac; popliteal and carotid. In a preferred embodiment, the starting vessel and target vessel comprise an external iliac. In an alternate embodiment, the starting vessel can comprise an artery and the target vessel can comprise a vein.

Step 510, the first step in the illustrated method of the present inventive concepts comprises procedural planning. This step comprises properly orienting the vein and the artery, meaning a clinician becomes familiar with the anatomical orientation of the vein and artery relative to each other. Understanding the orientation of the vessels with respect to one another can be achieved through analysis of one or more images provided by an imaging apparatus (e.g. a fluoroscope) such as imaging apparatus 190 of FIG. 2. In some embodiments, at least one of the vein or artery has a diameter of at least five millimeters proximate the fistula location. In another embodiment, both the vein and artery have a diameter of at least five millimeters proximate the fistula location.

In Step 520, the method comprises placing a first introducer into the vein. Preferably, the first introducer comprises an 11 French introducer having a beveled tip, such as introducer 110 of FIG. 2 described hereabove. In some instances, the beveled tip of the first introducer can be rotated during insertion into the vein. Rotation of the introducer can be helpful during insertion into the starting vessel due to the tendency of the beveled tip to lift and pull back. Additionally or alternatively, the introducer can be vibrated while it is advanced into the vein. Step 520 can further comprise pre-dilating the vein with a dilator, preferably a 13 French dilator, prior to placing the introducer into the vein. Additionally, a second introducer can be placed into the artery. Preferably, the second introducer comprises a 4 French introducer, such as introducer 130 described in FIG. 2 hereabove. The method further comprises placing a target wire into the second introducer and then into the artery such that the distal end of the target wire is positioned five to ten centimeters past the fistula location, and configured to serve as a visual reference to a clinician. The target wire, typically including a helical section, is advanced. The advancement can be combined with retracting the introducer such that the helical section of the wire is deployed at the targeted anastomotic site.

In Step 530, the method comprises performing angiographic orientation and selecting a fistula location. Choosing the fistula location can be based upon a lack of thrombus or other soft tissue occlusive matter at the vascular location, as well as lack of plaque or calcified matter. Preferably, the fistula location is chosen at a location where the vein is less than or equal to three millimeters apart from the artery. Techniques can be used to image the vein and artery in side-by-side configurations as well as overlapping (i.e. on top of each other in the image) orientations. Rotation of the imaging device 90° can modify the provided image from a side-by-side image to an overlapping image, and back again. In some embodiments, after a fistula location has been selected, a clinician can orient the fluoroscope such that the vein and artery are shown overlapping, such as with the vein on top of the artery. In some embodiments, the clinician can position a fluoroscope or other imaging device at an angle to the patient approximating 35° RAO.

In Step 540, the method comprises placing a vessel-to-vessel guidewire into the vein, such as while the vein and artery are imaged in an overlapping orientation, as described in Step 530 hereabove. A next step comprises placing a needle delivery device over the vessel-to-vessel guidewire and into the vein. The needle delivery device can comprise a marker, as described in FIG. 2 hereabove, such that a clinician can orient the marker toward the artery. The guidewire can be retracted and subsequently, the needle of the needle delivery device can be advanced toward the target wire and toward the artery. In some embodiments, the vessel-to-vessel guidewire can be placed through a dilator.

Prior to inserting the crossing needle into the artery, a clinician can aim the needle tip at the center of the artery to ensure desired engagement of the artery with the needle, such as by rotating the proximal end of the needle or a device containing the needle. In some embodiments, the needle or needle delivery device includes a proximal hub with a demarcation (e.g. a flat portion or a marker) positioned to indicate the orientation of a curved distal portion of the needle, such as is described in reference to needle deployment device 140 of FIG. 2 hereabove. In this operation, a clinician can torque or otherwise rotate the needle such that the direction of the needle curvature comes into view on the imaging apparatus (e.g. fluoroscope). Confirming the direction of needle curvature ensures that the needle is to be advanced in the desired direction, such as into the center of the artery. In some embodiments, a target wire is placed in the target vessel, such as target wire 170 of FIG. 2 described hereabove. Preferably, the needle comprises a curved tip, and the radius of curvature can be reduced if a clinician has difficulty in aiming the needle at the center of the target vessel prior to insertion. Conversely, the radius of curvature can be increased to sufficiently aim the needle tip at the center of the target vessel. In some embodiments, the needle delivery catheter is oriented as described in reference to FIG. 6 herebelow.

Additionally, a clinician can confirm that the distal portion of the vessel-to-vessel guidewire is located within the lumen of the artery. Also, the clinician can confirm the vessel-to-vessel guidewire is parallel with the target wire previously placed in the artery. A clinician can confirm that the needle is positioned within the target vessel by using a dye injection through the needle. Alternatively or additionally, a clinician can confirm that the needle is properly positioned in a target vessel by measuring the pressure in a distal portion of the needle, such as to confirm presence in an artery by confirming arterial pressure is recorded.

In some embodiments, the needle deployment device is placed into the artery and the guidewire is advanced from the artery into the vein via the crossing needle. In these embodiments, the anastomotic clip delivery catheter can also be advanced from artery to vein.

In Step 550, the method comprises placing an anastomotic clip at a fistula location. Prior to performing Step 550, placing an anastomotic clip at a fistula location, a user can retract the crossing needle while maintaining the position of the target wire. Next, the target wire can be removed from the second introducer. The target wire can also be removed after Step 550.

In Step 550, a user can position the vein and artery such that the vein and artery are slightly apart from each other on the image (e.g. not overlapping). In one embodiment, this can be achieved by rotating a fluoroscopy unit 45° to 90° after an overlapping image is obtained (e.g. an image obtained during a dual contrast injection of both the artery and vein).

Next, the tip of the clip deployment catheter (with a pre-loaded anastomotic clip) can be placed at the fistula site. In this step, a clinician can apply forward pressure and rotate the clip deployment catheter. The clip can comprise at least two distal arms and at least two proximal arms that can be deployed simultaneously or independently via a control located on the handle of the catheter.

Step 550 further comprises deploying the anastomotic clip in the fistula, such as is described in detail in reference to clip deployment catheter 150 of FIG. 2 hereabove. The clip distal arms are deployed by moving a control on the clip deployment catheter from a ready to deploy position to a first deployed position, which can be achieved by moving the control relatively parallel to the longitudinal axis of the handle. Prior to deploying the proximal arms of the clip, a clinician can retract the first introducer to the fistula location and seat the vein against the artery. The clip deployment catheter can comprise a marker located on its distal end. Using this marker, a clinician can pull the clip deployment catheter back such that the marker is aligned with the distal end of the first introducer.

In a next operation of STEP 550, the proximal arms can be queued to be deployed via moving the control from a first deployed position to a second ready to deploy position. The ready to deploy position can be achieved by moving the control in a direction perpendicular to the longitudinal axis of the handle. Subsequently, the proximal arms can deployed via moving the control from the second ready to be deployed position to the second deployed position via a motion parallel to the longitudinal axis of the handle. In this embodiment, the control includes a safety position comprising a ready to deploy position which can be transitioned by moving the control in a direction that is perpendicular to the axis of the handle. This control arrangement can prevent inadvertent deployment of the distal and/or proximal arms. After deployment of the proximal arms, a clinician can retract the first introducer from the anastomosis site, such as a retraction of approximately two to three centimeters, followed by retracting the clip deployment catheter.

The method can further comprise dilating the fistula via a balloon or other expandable member. For example, a clinician can track a balloon catheter over the target wire and inflate the balloon. In a typical embodiment, the balloon catheter comprises a diameter of four to five millimeters and can be inflated via a four millimeter by one and one half centimeter non-conforming balloon and indeflator device. The balloon then can be deflated and retracted out of the implant.

The method can further comprise verifying clip patency. This can be achieved via a contrast/saline solution injected into the second introducer. A clinician can then remove all devices once it is confirmed that the clip is positioned as desired.

The method can further comprise placing a second anastomotic clip, such as a second anastomotic clip 160 of FIG. 2 described hereabove. Alternatively or additionally, the method can further comprise creating a second flow pathway between, such as a second fistula created during the same clinical procedure or a subsequent clinical procedure. The second flow pathway can be between the same two vascular locations as the first flow pathway, or one or both of the second flow pathway vascular locations can be different (e.g. a different vein and/or artery).

Figure 6:
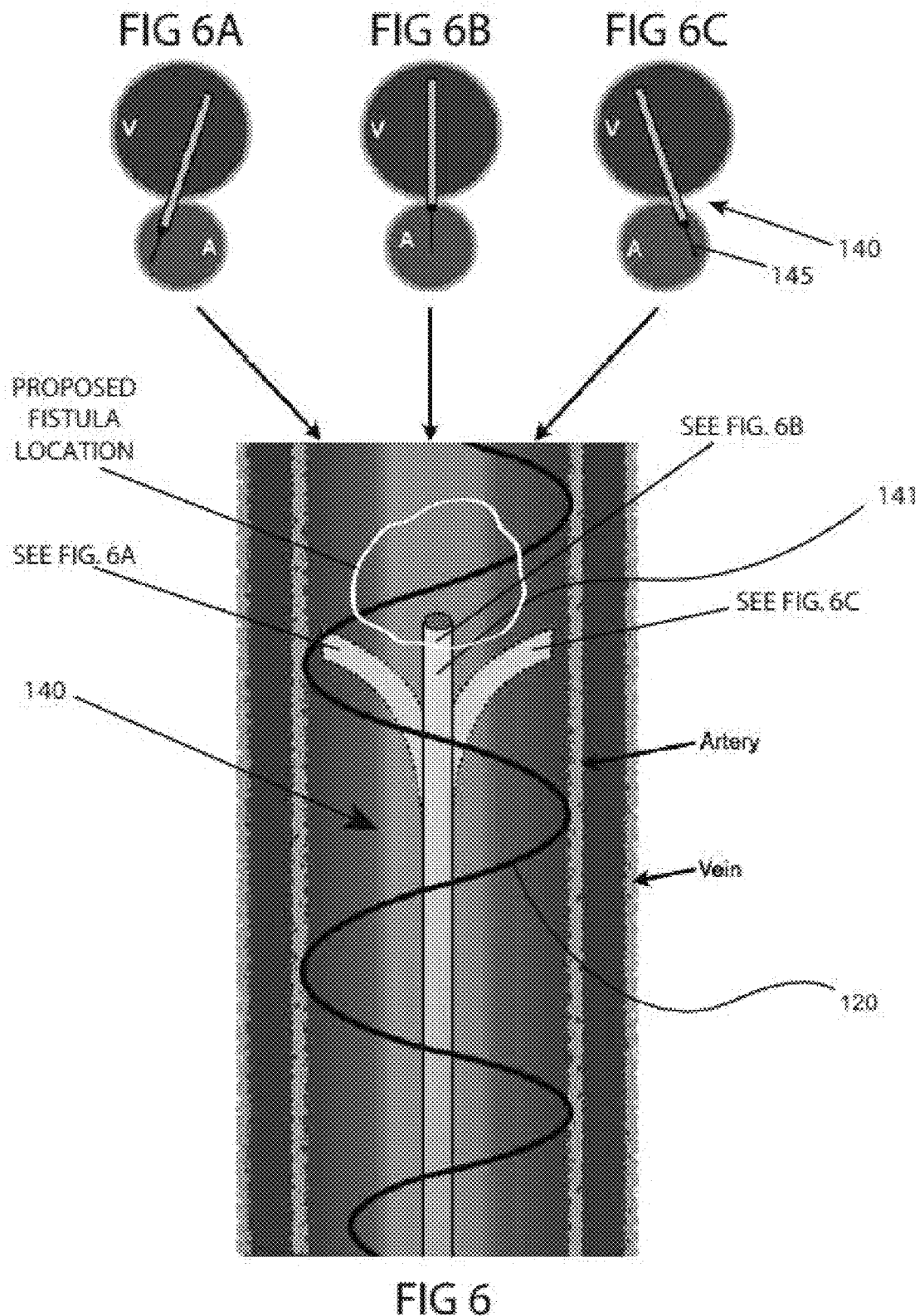
FIG. 6 is an angiographic view of a patient's vein and artery prior to advancement of a needle into the artery, consistent with the present inventive concepts.

Referring now to FIG. 6, an angiographic view of a patient's vein and artery prior to advancement of a needle into the artery is illustrated, such as may be performed in Step 540 of the method of FIG. 5 described hereabove, consistent with the present inventive concepts. In the illustrated embodiment, a clinician has oriented an imaging device (e.g. a fluoroscope or other imaging device of FIG. 1), such that the segments of vein and artery at a proposed fistula location are overlapping (i.e. on top of each other in the image). The clinician has placed a target wire 120 into a patient's artery such that the helical portion of wire 120 is positioned at the proposed fistula location. Additionally, needle deployment device 140 has been advanced intraluminally through the vein as shown such that its distal end is proximal to the proposed fistula location. A next step comprises advancing needle 145 toward the helical portion of wire 120 at the proposed fistula location.

Prior to insertion of needle 145 into the artery, a clinician can rotate needle deployment device 140 such that the direction of the needle deployment device 140 curvature is viewed (i.e. a non-linear, curved segment is visualized) on the imaging apparatus. Confirming the direction of curvature ensures that needle 145 is to be advanced in the desired direction, such as into the center of the artery. For example, if a clinician rotates needle deployment device 140 such that its tip is positioned as shown in FIG. 6A or 6C, a clinician will be aiming to an off-center location of the patient's artery. If a clinician rotates needle deployment device 140 such that its tip is positioned as shown if FIG. 6B, needle 145 will subsequently be advanced into the relative center of the patient's artery. The radius of curvature of a needle deployment device 140 can be reduced (e.g. by manual reshaping or by selected a different needle deployment device 140) if a clinician has difficulty in aiming needle 145 at the center of the artery prior to insertion. Conversely, the radius of curvature of needle deployment device 140 can be increased to create a more desirable needle 145 advancement trajectory.

Figure 7:
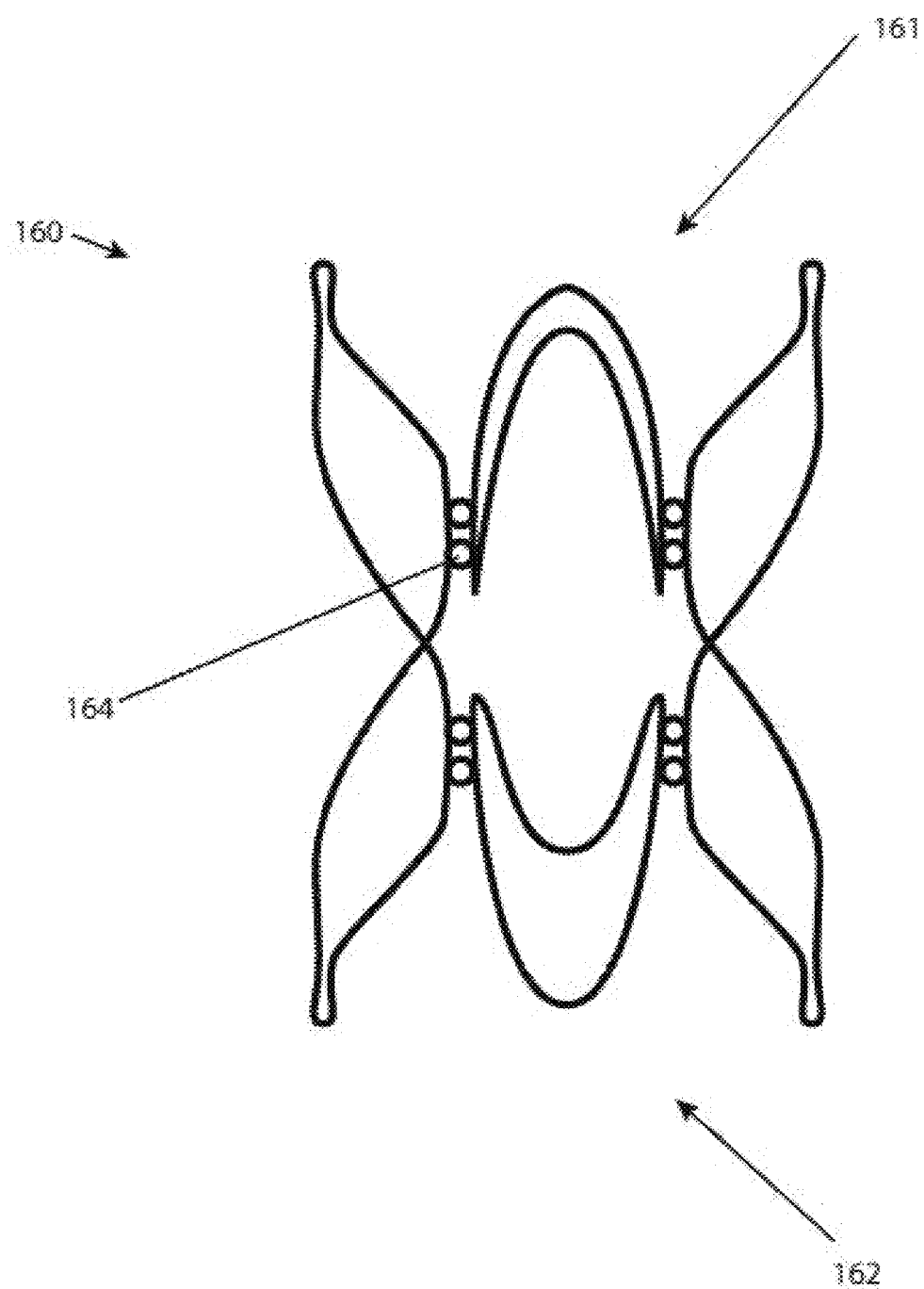
FIG. 7 is a perspective view of an anastomotic clip, consistent with the present inventive concepts.

Referring now to FIG. 7, a perspective view of an anastomotic clip is illustrated, consistent with the present inventive concepts. Clip 160 can comprise at least two distal arms 161 and at least two proximal arms 162. In the illustrated embodiment, clip 160 comprises four distal arms 161 and four proximal arms 162.

Clip 160 can be formed from a single tube of resilient material, such as nickel titanium alloy, spring steel, glass or carbon composites or polymers, or pseudoelastic (at body temperature) material such as nickel titanium alloy or comparable alloys and polymers, by laser cutting several closed-ended slots along the length of the tube (leaving the extreme distal and proximal edges of the tube intact) and cutting open-ended slots from the longitudinal center of the tube through the distal and proximal edges of the tube. The open-ended slots are cut between each pair of closed-end slots to form a number of loops joined at the center section by waist segments. Many other fabrication techniques can be utilized, for example, clip 160 can be made of several loops of wire welded together at the waist section.

After the tube is cut as described above, it is formed into its eventual resiliently expanded configuration. In this configuration, the loops turn radially outwardly from the center section, and evert toward the center plane of the center section, thus forming clinch members, i.e. distal arms 161 and proximal arms 162, in the form of arcuate, everted, petaloid frames at either end of the loop, extending from the generally tubular center section formed by waist segments. For clarity, the term everted is used here to mean that the arc over which the petaloid frame runs is such that the inside surface of clip 160 faces radially outwardly from the cylinder established by the tube.

Once clip 160 has resiliently expanded to the extent possible given its impingement upon the walls of the starting vessel and the target vessel, the center section can be further expanded by plastic deformation. This can be accomplished by inflating a balloon, not shown, within the center section and expanding the center section beyond its elastic or superelastic deformation range. By plastically deforming the center section of clip 160, the center section becomes more rigid and able to withstand the compressive force of the walls of the starting and target vessels.

As illustrated, the construction provides several pairs of longitudinally opposed (that is, they bend to come into close proximity to each other, and perhaps but not necessarily, touch) and aligned (they are disposed along the same longitudinal line) distal arms 161 and proximal arms 162. Overall, the petaloid frames of distal arms 161 form a "corolla," analogous to the corolla of a flower, flange or rivet clinch, which impinges on the starting vessel wall and prevents expulsion into the target vessel, and the petaloid frames of proximal arms 162 form a corolla, flange or rivet clinch (this clinch would be analogous to a rivet head, but it is formed like the clinch after insertion of the rivet), which impinges on the target vessel wall and prevents the expulsion of clip 160 into the target vessel. Also, the central section forms a short length of rigid tubing to keep the fistula open. The resilient apposition of the at least two distal arms 161 and at least two proximal arms 162 will securely hold clip 160 in place by resiliently clamping the walls of the starting vessel and the target vessel, even over a considerable range of wall thickness or "grip range."

The respective lengths of arms 161 and 162 can be variably sized to maximize or optimize the stability of clip 160 with respect to the vessels when deployed between adjacent vessels. Moreover, varying the lengths of the respective arms can further provide additional advantages. For instance, the arms which are shortened in length can facilitate the positioning and securement of clip 160 between the vessels by allowing for the relatively shorter member to swing into position within the vessel lumen during deployment, as described in further detail below. Additionally, a shorter member can provide for a minimized implant size when placed against the vessel interior wall for securement as well as a mitigating any physiologic reaction to the implant, e.g., a reduction in thrombosis, etc. Additionally, arms 161 and/or 162 which are lengthened relative to other arms can provide for increased clip stability by increasing the amount of force applied against the tissue walls.

Moreover, arms having different lengths can additionally place the adjacent vessels in tension such that the vessel walls are drawn towards one another and arms 161 and/or 162 contact the vessel luminal walls to stabilize not only clip 160 within the vessels but also the vessels with respect to one another. Additionally, having one or more arms, such as distal arms 161, sized to have a length shorter than its respective apposed clinch member can also facilitate the deployment and/or positioning of distal arms 161 within the vessel since the shorter length clinch members can more easily "swing" through an arc within the vessel lumen without contacting the interior walls. Arms with differing lengths can further be configured to align along different planes when deployed to facilitate vessel separation, if so desired.

Clip 160 can further comprise at least one marker, not shown, configured to rotationally position the clip at the fistula location. For example, a marker can be oriented toward the target vessel prior to deployment of clip 160. Alternatively or additionally, a marker can be oriented based upon a patient image, e.g. a real-time fluoroscopy image. In yet another embodiment, clip 160 can comprise at least one marker configured to longitudinally position the clip at the fistula location. A marker can indicate the distal and/or proximal end of clip 160.

Clip 160 can further comprise holes 164 configured to engage a clip delivery catheter projection such as to allow the shaft of the clip deployment catheter, not shown, to be retracted while clip 160 remains positioned in the distal portion of the shaft. In one embodiment, holes 164 are constructed and arranged about the clip asymmetrically such that clip 160 can be attached in the proper orientation.

Figure 8:
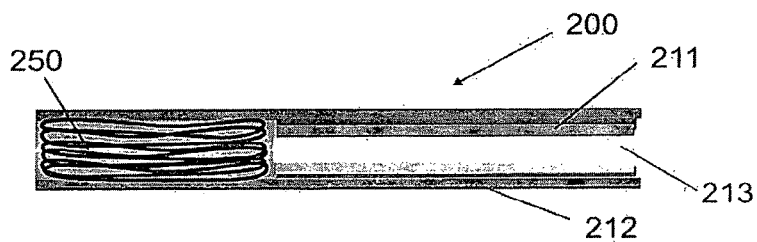
FIG. 8 is a cross sectional view of an anastomotic clip deployment device consistent with the present invention.

FIG. 8 depicts apparatus 200, an anastomotic clip deployment apparatus consistent with the present invention. Apparatus 200 is a flexible, catheter device, which includes a sliding core, core 211, which has a lumen, lumen 213, from its proximal end, not shown, to its distal end, to allow placement over a guidewire. Apparatus 200 includes outer sheath 212, which surrounds and slidingly receives core 211. Located at or near the distal end of apparatus 200, is a preloaded anastomotic clip, clip 250, which is a self-expanding device constrained by outer sheath 212 which can be deployed to secure and create a fistula between an artery and a vein, such as the Aorta and the IVC. Clip 250 can be deployed by advancing core 211 forward while maintaining outer sheath 212 in a relatively fixed position, by retracting sheath 212 while maintaining core 211 in a relatively fixed position, or by both advancing core 211 and retracting outer sheath 212. A deployment trigger and trigger mechanism, described herein, may be incorporated into apparatus 200 such that the retraction and/or advancement steps, are accomplished by activating the trigger, such that timing, relative timing and advancement and retraction distances are predetermined by the trigger mechanism. In a preferred embodiment, some amount of advancement and retraction are accomplished simultaneously.

Figure 9:
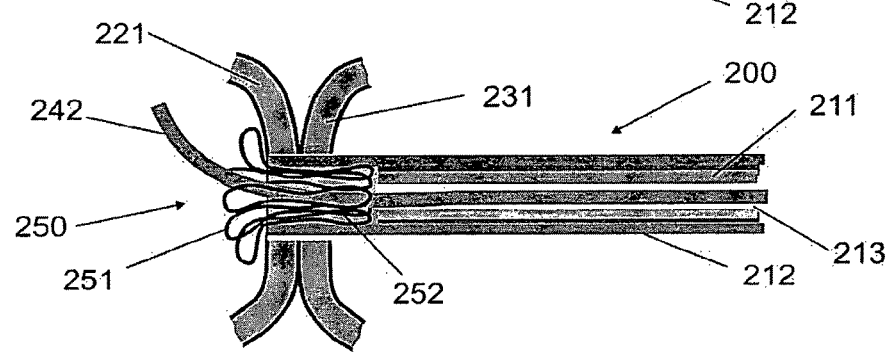
FIG. 9 is a cross sectional view of an anastomotic clip deployment device shown at a fistula creation site prior to full deployment of an anastomotic clip.

FIG. 9 depicts apparatus 200 deployed over a guidewire, guidewire 242, which can be placed similar to guidewire 170 described herein, such that it passes from the Aorta to the IVC. Guidewire 242 is shown passing through arterial wall 231, such as the wall of the Aorta, and venous wall 221, such as the wall of the IVC. Outer sheath 212 is shown passing through both arterial wall 231 and venous wall 221 to assist in the deployment of clip 250. In order to cross through the vessel walls, apparatus 200 may include a flow path enlarging element such as an integrated balloon element and/or apparatus 200 may include a dilating slope on one or more distal ends. Apparatus 200 of FIG. 9 depicts clip 250 being placed from artery to vein, however it should be appreciated that a vein to artery placement can be similarly accomplished by apparatus 200 and would result in a similarly placed clip 250.

In FIG. 9, clip 250 is partially deployed, to partially deploy the self-expanding distal end 251 of clip 250. Deployment is initiated such as by advancing core 211 while maintaining outer sheath 212 in a fixed position, by retracting sheath 212 while maintaining core 211 in a fixed position, or by both, perhaps simultaneously, advancing core 211 and retracting sheath 212. Proximal end 252 of clip 250 remains constrained by outer sheath 212. During the deployment process, apparatus 200 or any portion of apparatus 200 can be retracted while injecting contrast medium. Contrast medium can be injected through apparatus 200, or through a venous catheter or separate arterial catheter. Contact of the distal flange of clip 250 can be confirmed by visualizing bulging of either or both the venous wall 221 and the arterial wall 231 during a contrast medium injection.

Figure 10:
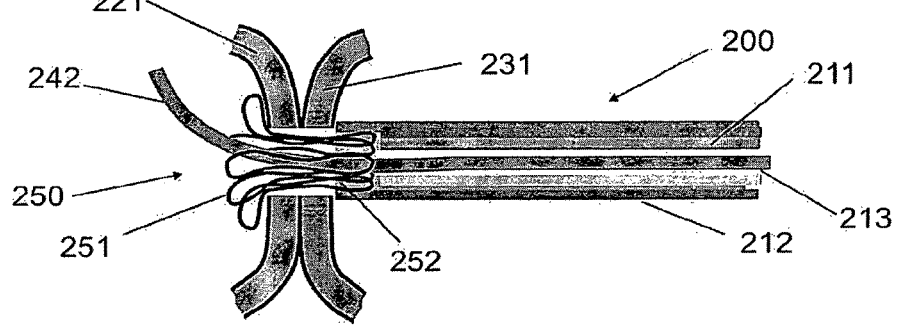
FIG. 10 is a cross sectional view of an anastomotic clip deployment device shown at a fistula creation site prior to full deployment of an anastomotic clip.

In FIG. 10, clip 250 has been further deployed, and outer sheath 212 retracted to expose venous wall 221 and arterial wall 231. In an alternative embodiment, outer sheath 212 does not pass through arterial Wall 231 and/or venous wall 221 and clip 250 is pushed through both walls during deployment.

Figure 11:
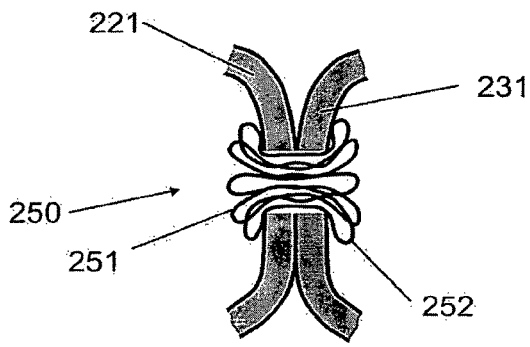
FIG. 11 is a cross sectional view of a fistula creation site with an anastomotic clip deployed.

FIG. 11 depicts a fully deployed clip 250, providing an anastomotic connection between arterial wall 231 and venous wall 221 such as to provide a flow path, or fistula between an artery and vein such as the Aorta and IVC. Clip 250 can provide numerous functions as has been described herein including but not limited to prevention of blood leakage outside the two vessels, maintenance of the flow path between the two vessels, and other functions. In FIG. 11, guidewire 242 has been removed and the procedure can be considered complete. In a preferred embodiment, guidewire 242 remains in place, and subsequent operations can be performed to enhance the outcomes and/or therapeutic benefits of the procedure, or to complete one or more other interventional procedures such as those performed in either the starting vessel, or target vessel by way of the starting vessel.

During retraction of apparatus 200 or one of its components, a balloon integrated on the core 211 of apparatus 200, not shown, may be inflated to help bias clip 250 in an open position during retraction. This particular embodiment may also be important if retro-peritoneal bleeding is suspected. Prior to complete retraction, a contrast medium injection from the arterial side can be used to assess blood flow through the fistula. In a preferred embodiment, guidewire 240 is not removed until proper flow and/or sufficient therapeutic benefit are confirmed. If flow is determined to be insufficient, or even too great, subsequent procedures can be employed to change the flow characteristics, such procedures described in more detail herein.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A system for treating hypertension in a patient, comprising:
a needle delivery device constructed and arranged to place a vessel-to-vessel guidewire from a starting vessel to a target vessel;
a flow creation device constructed and arranged to be advanced over the vessel-to-vessel guidewire and to create a flow pathway between the starting vessel and the target vessel;
wherein the system is constructed and arranged to cause a reduction in diastolic pressure,
wherein the flow creation device comprises a clip deployment catheter comprising an inner shaft, an anastomotic clip positioned over the inner shaft, a distal tip coupled to the inner shaft, and an outer sheath covering the anastomotic clip when ready to deploy, the anastomotic clip comprising at least one distal arm and at least one proximal arm,
wherein the clip deployment catheter comprises a handle and the handle comprises a control constructed and arranged to be moved by an operator to retract the outer sheath to allow the anastomotic clip to deploy,
wherein the handle is constructed and arranged to allow an operator to move the control from a first ready to deploy position to a first deployed position to cause the outer sheath to retract a first distance relative to the distal tip to allow the at least one distal arm to deploy while the clip is held stationary relative to the distal tip,
wherein the handle is further constructed and arranged to allow the operator to move the control from the first deployed position to a second ready to deploy position, and
wherein the handle is further constructed and arranged to allow the operator to move the control from the second ready to deploy position to a second deployed position to cause the outer sheath to retract a second distance relative to the distal tip to allow the at least one proximal arm to be deployed while the clip is held stationary relative to the distal tip.

2. The system of claim 1 wherein the control comprises a button.

3. The system of claim 1 wherein the handle comprises a safety position for the control.

4. The system of claim 3 wherein the handle comprises a longitudinal axis and wherein the control is constructed and arranged to be moved relatively perpendicular to said longitudinal axis to transition from the safety position to the first ready to deploy position.

5. The system of claim 1 wherein the clip comprises at least two distal arms.

6. The system of claim 1 wherein the handle comprises a longitudinal axis and wherein the control is moved relatively parallel to said longitudinal axis to transition from the first ready to deploy position to the first deployed position.

7. The system of claim 6 wherein the control is moved relatively perpendicular to the longitudinal axis to transition from the first deployed position to the second ready to deploy position.

8. The system of claim 1 wherein the clip comprises at least two proximal arms.

9. The system of claim 6 wherein the control is moved relatively parallel to said longitudinal axis to transition from the second ready to deploy position to the second deployed position.

10. The system of claim 1 wherein the clip deployment catheter is constructed and arranged such that movement of the control to the second position causes a tactile feedback event to occur.

11. The system of claim 1 further comprising a venous system introducer, wherein the venous system introducer comprises a distal portion and an expandable element mounted to the distal portion.

12. The system of claim 11 wherein the expandable element is constructed and arranged to prevent inadvertent advancement of the introducer into the target vessel.

* * * * *